US008658572B2

(12) United States Patent
Albert et al.

(10) Patent No.: US 8,658,572 B2
(45) Date of Patent: Feb. 25, 2014

(54) WHOLE PROTEOME TILING MICROARRAYS

(75) Inventors: Tom Albert, Verona, WI (US); Todd Richmond, Madison, WI (US); Matthew Rodesch, Stoughton, WI (US); Klaus-Peter Stengele, Pleiskirchen (DE); Jochen Bühler, Waldkraiburg (DE)

(73) Assignee: Roche NimbleGen, Inc., Madison, WI (US)

( * ) Notice: Subject to any disclaimer, the term of this patent is extended or adjusted under 35 U.S.C. 154(b) by 0 days.

(21) Appl. No.: 13/419,197

(22) Filed: Mar. 13, 2012

(65) Prior Publication Data

US 2012/0245057 A1 Sep. 27, 2012

Related U.S. Application Data

(60) Provisional application No. 61/454,214, filed on Mar. 18, 2011.

(51) Int. Cl.
*C40B 40/10* (2006.01)

(52) U.S. Cl.
USPC .......................................................... 506/18

(58) Field of Classification Search
None
See application file for complete search history.

(56) References Cited

U.S. PATENT DOCUMENTS

2009/0176664 A1* 7/2009 Chu ................................ 506/18

FOREIGN PATENT DOCUMENTS

WO 2008151146 A2 12/2008

OTHER PUBLICATIONS

Cheng, Yu Chien et al., "Chip Printer," Proceedings of the WSEAS, pp. 19-22 (2010).
Foder, S.P.A. et al., "Multiplexed biochemical assays with biological chips," Nature 364:555-556 (1993).
Foder, S.P.A. et al., "Light-Directed, Spatially Adressable Parallel Chemical Synthesis," Science 251:767-773 (1991).
Marthandan, N. et al., "Construction and Evaluation of an Automated Light Directed Protein-Detecting Microarray Synthesizer," IEEE Transactions of Nanobioscience 7:20-27 (2008).
Singh-Gasson, S. et al., "Maskless fabrication of light-directed oligonucleotide microarrays using a digital micromirror array," Nature Biotechnology 17:974-978 (1999).

* cited by examiner

*Primary Examiner* — Christopher M Babic
*Assistant Examiner* — Karen S Weiler
(74) *Attorney, Agent, or Firm* — Quarles & Brady LLP

(57) ABSTRACT

The present invention relates to a microarray comprising at least 50,000 oligopeptide features per $cm^2$ where the oligopeptide features represent at least 50%, 60%, 70%, 80%, 90%, 95%, 99%, or 100% of the proteome of a virus or an organism. The present invention further relates to methods for the synthesis of such microarrays and methods of using microarrays comprising at least 50,000 oligopeptide features per $cm^2$. In an embodiment of the invention, the oligopeptide features represent proteins expressed in the same species, wherein the oligopeptide features are presented in a tiling pattern representing at least about 5,000 to-at least about 25,000 proteins expressed in a species. In some embodiments, the oligopeptide microarray features represent proteins expressed in the same species, wherein the microarray features are present in a tiling pattern that represents at least about 5,000 to at least about 50,000 expressed proteins.

20 Claims, 12 Drawing Sheets

Fig. 2

FIG. 2A    620 - RLVNPPPRSSGNAATSGNAATKIPTPIVGV  - 649
                 RLVNPPPRSSGN
                  LVNPPPRSSGNA
                ⌐⌐VNPPPRSSGNAA
    1 aa step    NPPPRSSGNAAT FIG. 2B    RLVNPPPRSSGNAATSGNAATKIPTPIVGV
           RLVNPPPRSSGN
               NPPPRSSGNAAT
              ⌐⌐  PRSSGNAATSGN
              ⌐⌐      SGNAATSGNAAT
           3 aa step FIG. 2C    RLVNPPPRSSGNAATSGNAATKIPTPIVGV
           RLVNPPPRSSGN
                 PRSSGNAATSGN
                       AATSGNAATKIP
              ⌐_____⌐    AATKIPTPIVGV
               6 aa step

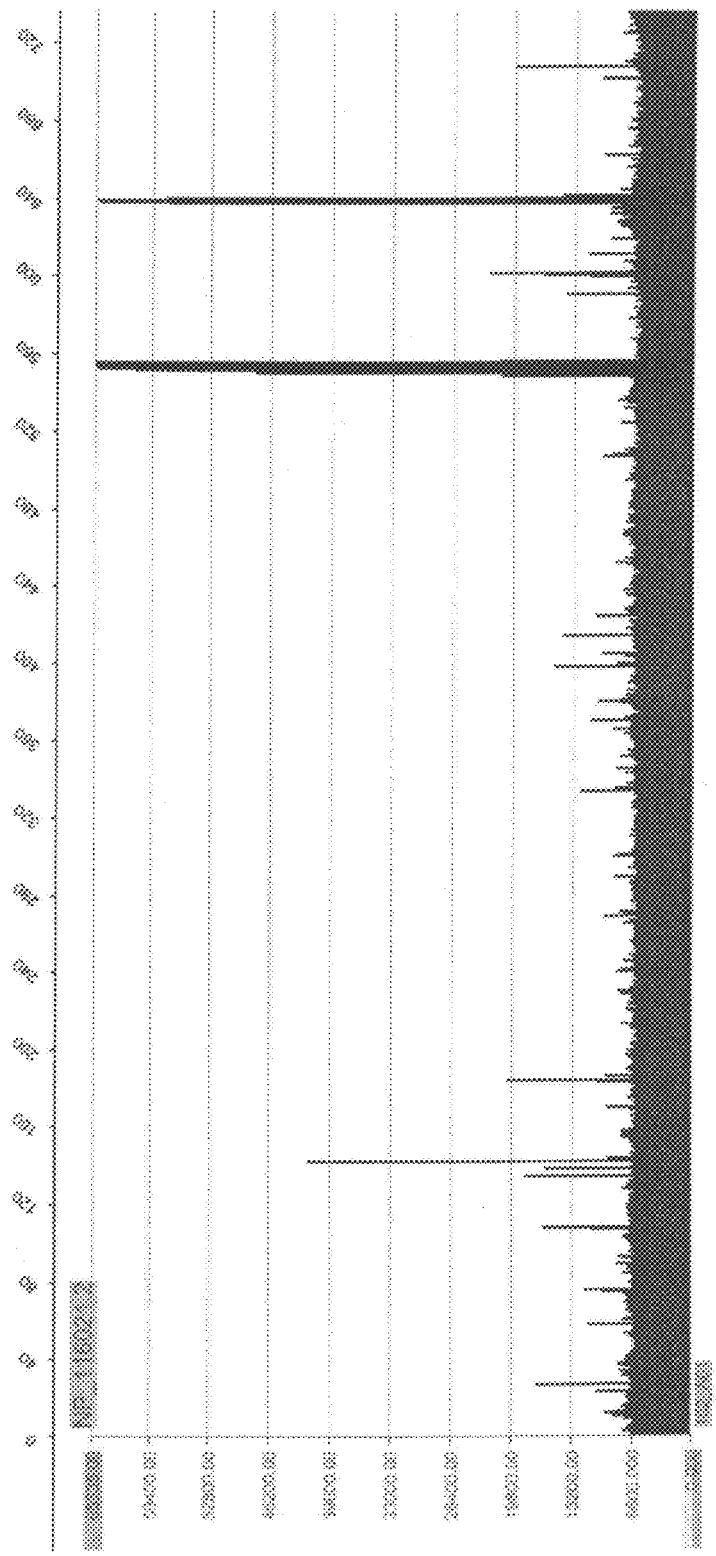

FIG. 4

| Antibody | Epitope(s) | | |
|---|---|---|---|
| HPA007244 | QAVASIAGGIRNGYD | ITSENVAERFOIS | |
| HPA006198 | GCTOVQTAIEGNSLG | QMPIIIAGNDQQ | |
| HPA005552 | SRPTPSDMAIV | | |
| HPA001399 | SLLPGHVQAYQEAVK | HTLEDQALYN | |
| HPA000525 | NDLIERIQVDAY | | |
| HPA008333 | SVLQNQGREMMLVTSGAV | | |
| HPA005554 | LDAAVTPOPS | | |
| HPA010793 | WGGEDDDIAY | | |
| HPA001328 | FRGDGGSTTGLSATPPA | | |
| HPA001198 | KHMTRSQAEQLLK | | |
| HPA005992 | RRERRFGRDMETIGPA | | |
| HPA002384 | FWEQDFHRDMEALNVLP | | |
| HPA001223 | ERIXOTLKPODTI | ILQQCDGKLDMLV | |
| HPA001354 | QCQAIDDLMPAQK | | |
| HPA008833 | GKNKQSLDAVE | | |
| HPA001566 | SVGMIAGGTGIT | AIMKDPDDHTV | MIQYACLPNLDH |
| HPA006793 | WTSFLSGVNI | | |
| HPA006461 | QLKMVVPGLDGAQI | | |
| HPA006148 | EIXGGIRRIQTRGE | | |
| HPA006237 | HISPQAKALLQDK | DPLGKDGYQLRQGD | IGGPRSYTIAVA |
| HPA004701 | HPCRQPDTPT | | |
| HPA001249 | ATQCISDQKLNEGHT | | |
| HPA003494 | WWKAQSLTTGQEG | RQLLAPGNT | |
| HPA006723 | CNPDDMARDLEQ | | |
| HPA001334 | SFVPWQPRFMIHMCPST | KEVFSGIKNSNE | RYSWDCSPLSMFRRH |
| HPA001231 | NTERTIYVRDPTS | | |
| HPA008247 | WPESASSPPV | | |
| HPA001240 | DGGLRHWLRQNLP | EPRDGEPGIH | |
| HPA000704 | NSINTEEVIN | | |
| HPA008467 | LSTLGIVFQG | PISSCDTGTMANCERT | IKPDGVQRGLVGE |
| HPA001303 | QKLODIQRAMELLSACQ | | |
| HPA007308 | TTGGSUSMYS | LTYSIGHTPADARI | LFDLNFQAGFLMKK |
| HPA000571 | LQERAVLGANDP | TAIRPHGIFGPRDPQLVP | |
| HPA006314 | ISDGPSVSALTNGFDTPEERYQ | YDEKESQANGAGA | |
| HPA006277 | SLDSLPQAVREFLE | QRDTVPIPKTGLSQLGRW MSEEDFEK | FPGCMKGRTMYVIPFSM |
| HPA002645 | GSNYWRNRVMMVAK | | |
| HPA003230 | PTLKIFRDDEEAGAYDQPRTADGIVSHLKKQAGPASVPLKTEEEFKKPISDKDASIVPFDDSPSEAHSFL KAASNLRDNYRFAHT | | |
| HPA003982 | TLCKPAPLTGTLEV | DSRPPFLSRPA | LYSKGSLSG |
| HPA006782 | PETRTVAVKQLGVNPSTIGTQ | LVNGIHPLTLRWEET | QPDIPPGTPLVQDE |
| HPA002947 | LEPMAAKAWDKESE | | |
| HPA003049 | KFDWTFEQTVETAIT | | |
| HPA006700 | QTEARDLVERCMRVL | | |
| HPA007981 | DPHQRLTAKQVLQHPWVTQKD | QLKPIESSILQRRVRKLPS TTL | |
| HPA002867 | SCAMNINGGNTLACTR | TNLNKVSKIYPLPH | VPDLSNPYAQ |
| HPA001401 | PVQGHNFEQKESNGPVKVWGSI KGL | EFODNTAGCTSAGPHFN | |
| HPA003323 | IGLDTTIMMRSIPL | GFDQQMSSMV | DSTTKEDTGT |
| HPA005993 | KQTIGNSCOT | DGHLYELDGRMPFPVN | |
| HPA004769 | TQSKEAFAIGL | VARMIIEALD | SMDSPYKVLTEQ |
| HPA006666 | SAKRHLAEQFAVGEITD | KVESDNGPLFTELK | NGKSYRFMIMDRFGSDLQK |
| HPA006988 | SETFEKSRLYQLDKS | | |

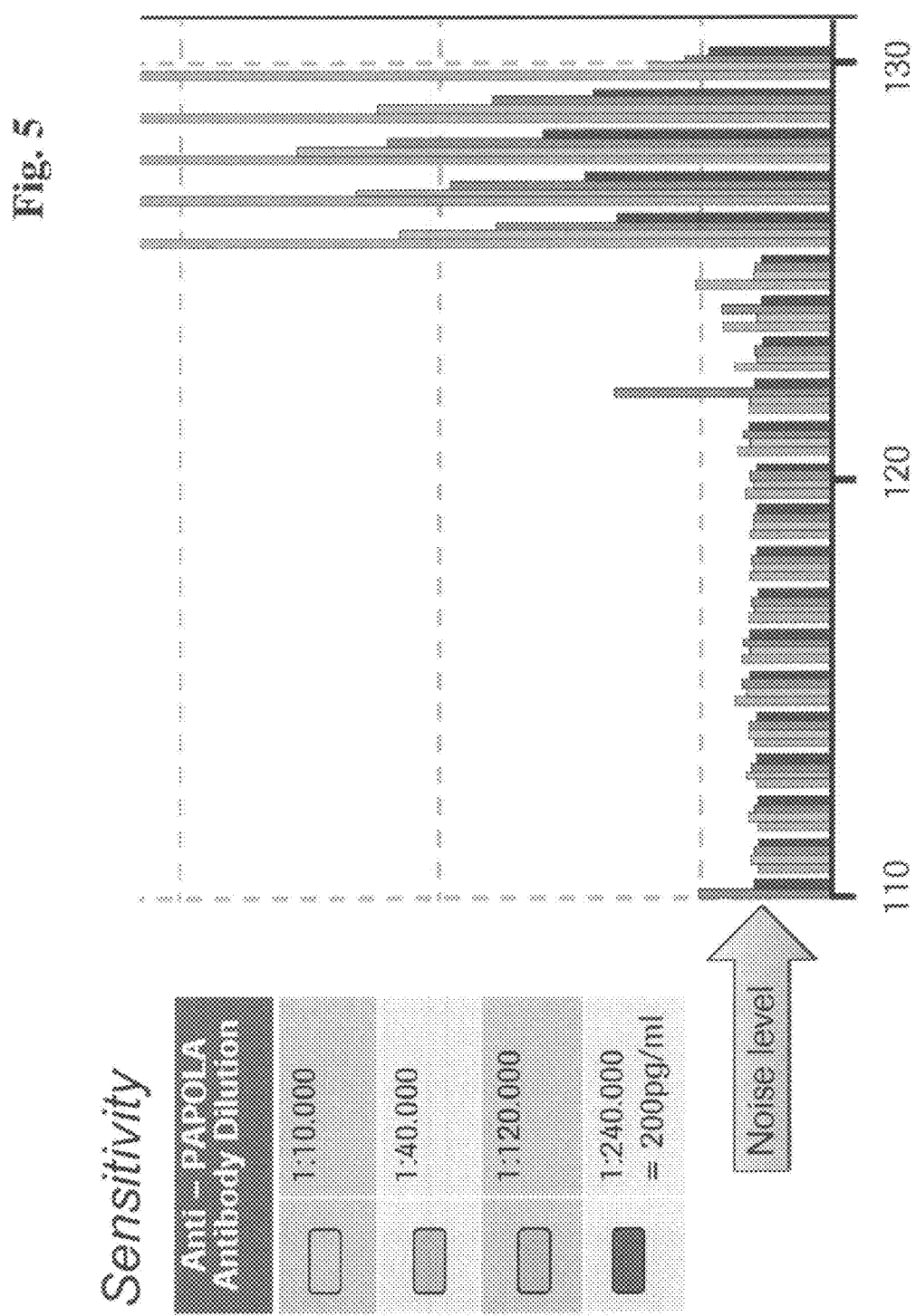

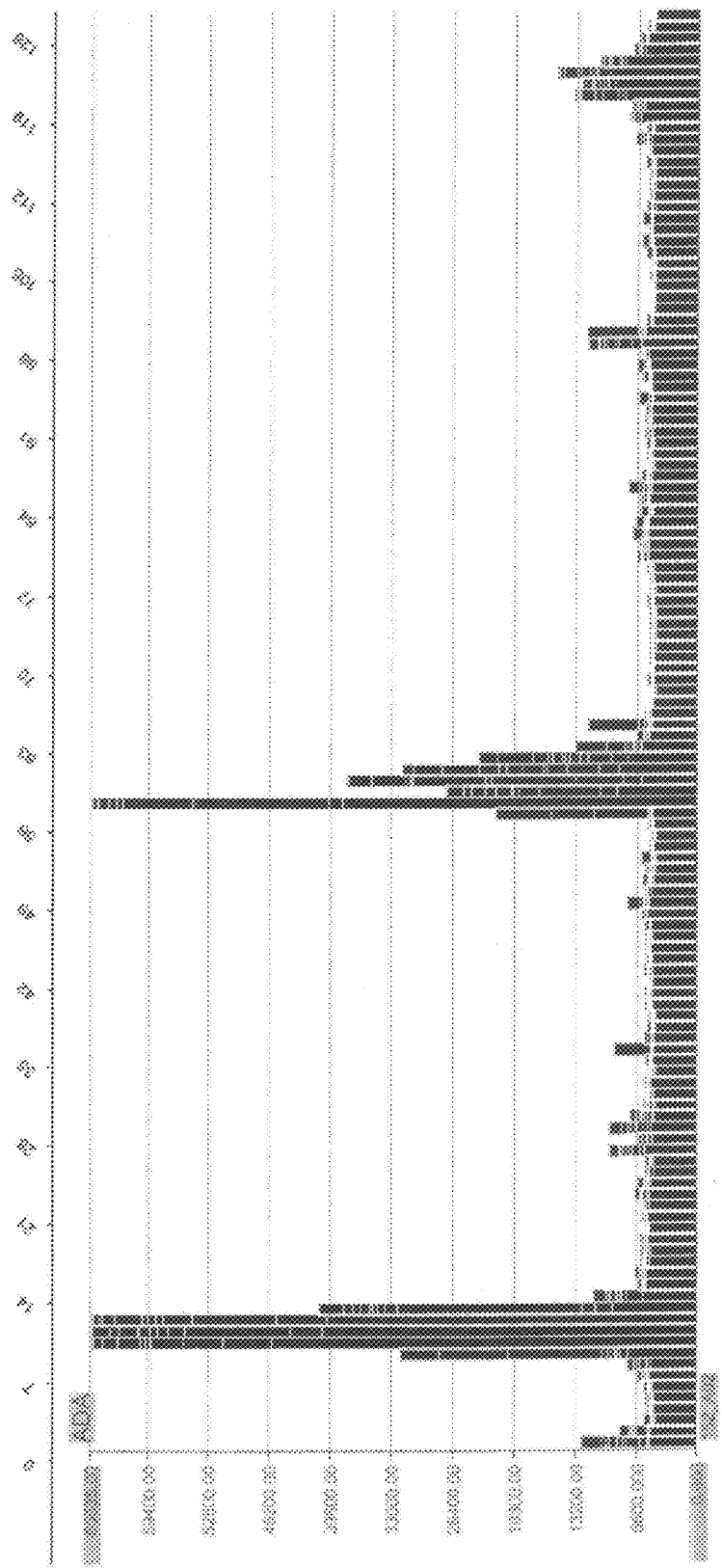

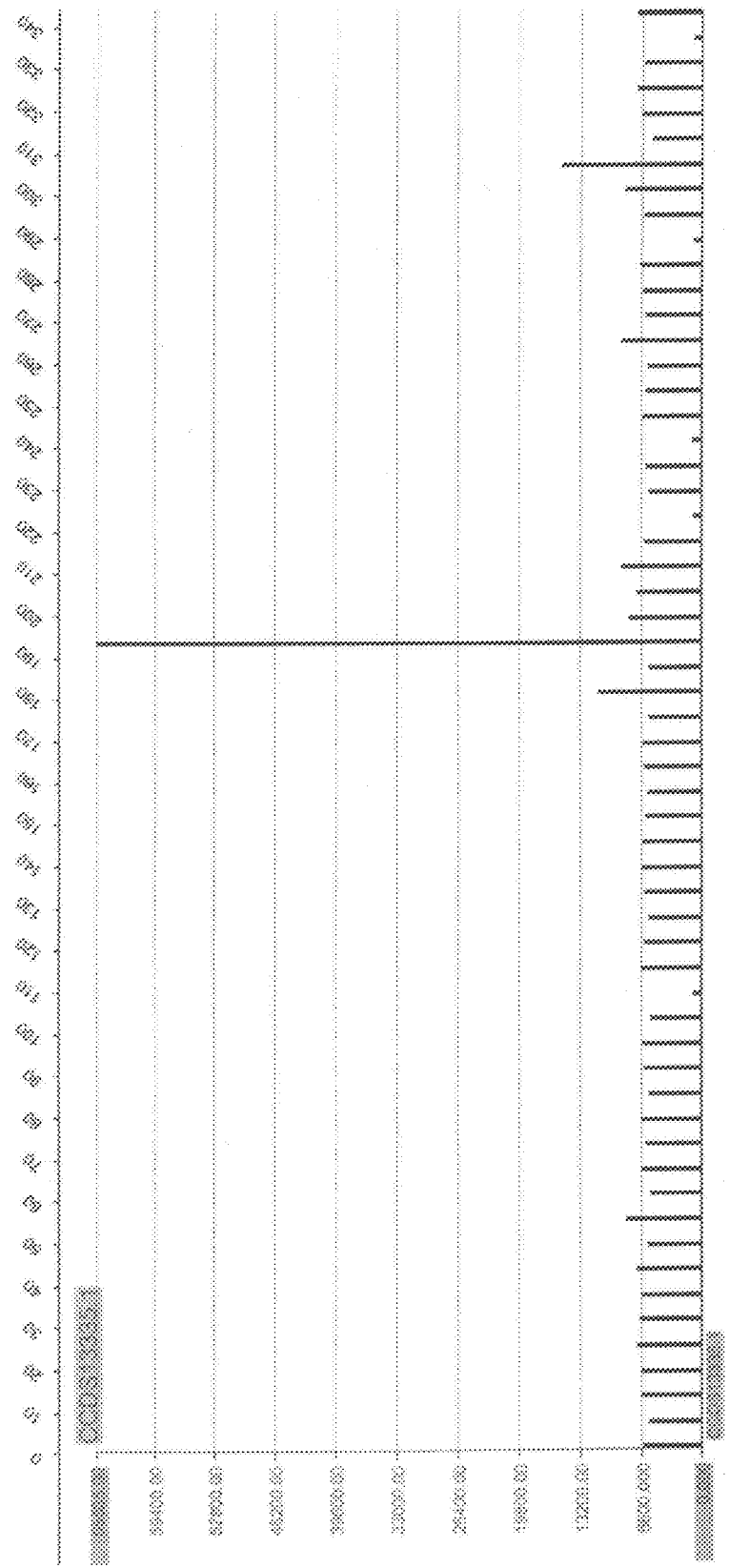

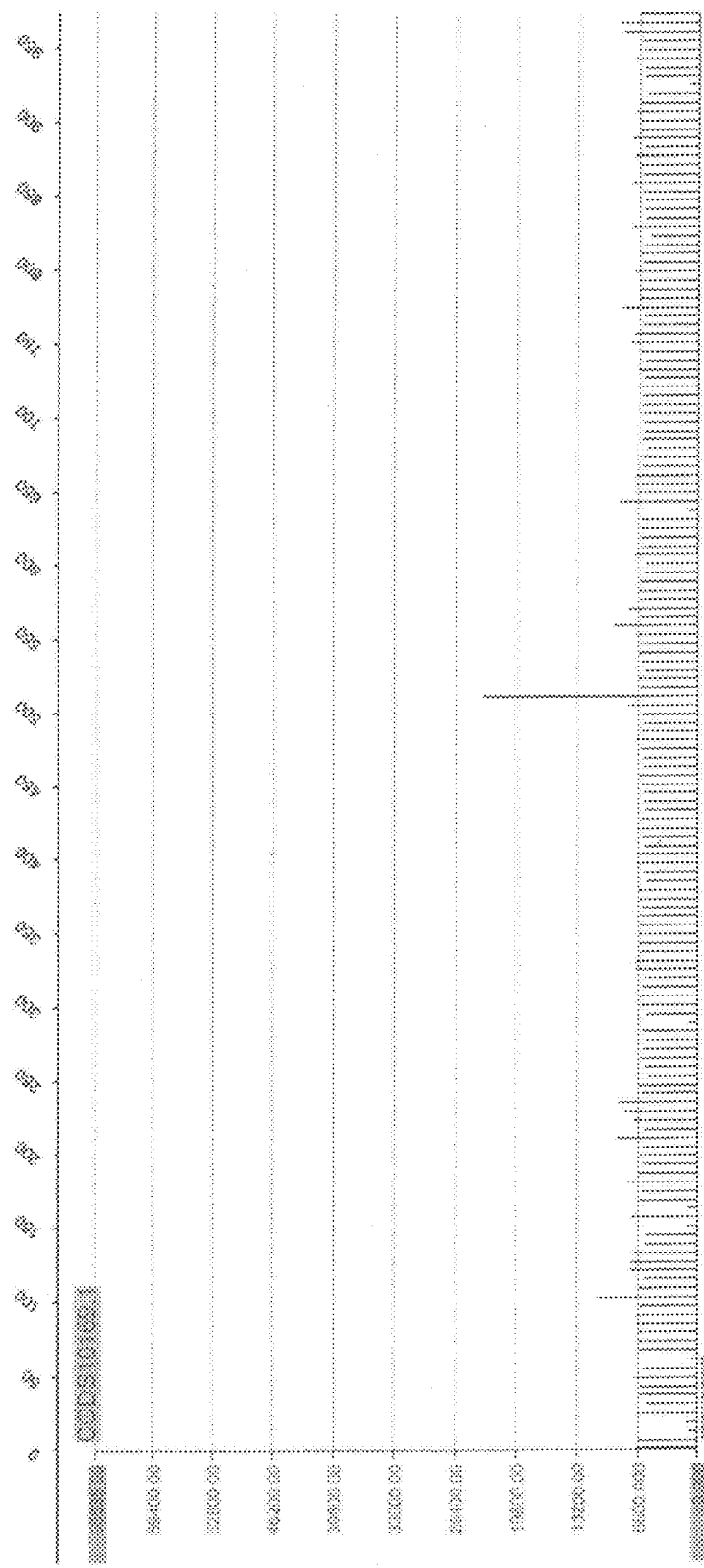

SEQUENCE LISTING

```
<160> NUMBER OF SEQ ID NOS: 16

<210> SEQ ID NO 1
<211> LENGTH: 30
<212> TYPE: PRT
<213> ORGANISM: Artificial Sequence
<220> FEATURE:
<223> OTHER INFORMATION: poly(A) polymerase alpha epitope

<400> SEQUENCE: 1

Arg Leu Val Asn Pro Pro Pro Arg Ser Ser Gly Asn Ala Ala Thr Ser
1               5                   10                  15

Gly Asn Ala Ala Thr Lys Ile Pro Thr Pro Ile Val Gly Val
            20                  25                  30

<210> SEQ ID NO 2
<211> LENGTH: 18
<212> TYPE: PRT
<213> ORGANISM: Artificial Sequence
<220> FEATURE:
```

-continued

```
<223> OTHER INFORMATION: poly(A) polymerase alpha epitope

<400> SEQUENCE: 2

Asn Ser Ser Gly Ser Ser Gln Gly Arg Asn Ser Pro Ala Pro Ala Val
1               5                   10                  15

Thr Ala

<210> SEQ ID NO 3
<211> LENGTH: 13
<212> TYPE: PRT
<213> ORGANISM: Artificial Sequence
<220> FEATURE:
<223> OTHER INFORMATION: poly(A) polymerase alpha epitope

<400> SEQUENCE: 3

Asn Ala Ala Thr Lys Ile Pro Thr Pro Ile Val Gly Val
1               5                   10

<210> SEQ ID NO 4
<211> LENGTH: 12
<212> TYPE: PRT
<213> ORGANISM: Artificial Sequence
<220> FEATURE:
<223> OTHER INFORMATION: poly(A) polymerase alpha epitope

<400> SEQUENCE: 4

Ala Thr Gln Pro Ala Ile Ser Pro Pro Pro Lys Pro
1               5                   10

<210> SEQ ID NO 5
<211> LENGTH: 18
<212> TYPE: PRT
<213> ORGANISM: Artificial Sequence
<220> FEATURE:
<223> OTHER INFORMATION: poly(A) polymerase alpha epitope

<400> SEQUENCE: 5

Asn Ser Ser Gly Ser Ser Gln Gly Arg Asn Ser Pro Ala Pro Ala Val
1               5                   10                  15

Thr Ala

<210> SEQ ID NO 6
<211> LENGTH: 14
<212> TYPE: PRT
<213> ORGANISM: Artificial Sequence
<220> FEATURE:
<223> OTHER INFORMATION: poly(A) polymerase alpha epitope

<400> SEQUENCE: 6

Asn Ala Ala Thr Lys Ile Pro Thr Pro Ile Val Gly Val Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: poly(A) polymerase alpha epitope

<400> SEQUENCE: 7

Ala Thr Gln Pro Ala Ile Ser Pro Pro Pro Lys Pro
1               5                   10

<210> SEQ ID NO 8
<211> LENGTH: 18
<212> TYPE: PRT
```

```
<213> ORGANISM: Artificial Sequence
<220> FEATURE:
<223> OTHER INFORMATION: poly(A) polymerase alpha epitope

<400> SEQUENCE: 8

Leu Asn Ser Ser Gly Ser Ser Gln Gly Arg Asn Ser Pro Ala Pro Ala
1               5                   10                  15

Val Thr

<210> SEQ ID NO 9
<211> LENGTH: 12
<212> TYPE: PRT
<213> ORGANISM: Artificial Sequence
<220> FEATURE:
<223> OTHER INFORMATION: poly(A) polymerase alpha epitope

<400> SEQUENCE: 9

Asn Ala Ala Thr Lys Ile Pro Thr Pro Ile Val Gly
1               5                   10

<210> SEQ ID NO 10
<211> LENGTH: 10
<212> TYPE: PRT
<213> ORGANISM: Artificial Sequence
<220> FEATURE:
<223> OTHER INFORMATION: poly(A) polymerase alpha epitope

<400> SEQUENCE: 10

Gln Pro Ala Ile Ser Pro Pro Pro Lys Pro
1               5                   10

<210> SEQ ID NO 11
<211> LENGTH: 14
<212> TYPE: PRT
<213> ORGANISM: Artificial Sequence
<220> FEATURE:
<223> OTHER INFORMATION: ADA protein epitope

<400> SEQUENCE: 11

Ser Leu Leu Pro Gly His Val Gln Ala Tyr Gln Glu Ala Val
1               5                   10

<210> SEQ ID NO 12
<211> LENGTH: 15
<212> TYPE: PRT
<213> ORGANISM: Artificial Sequence
<220> FEATURE:
<223> OTHER INFORMATION: ADA protein epitope

<400> SEQUENCE: 12

His Thr Leu Glu Asp Gln Ala Leu Tyr Asn Arg Leu Gln Glu Asn
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: ADA protein epitope

<400> SEQUENCE: 13

Ser Leu Leu Pro Gly His Val Gln Ala Tyr Gln Glu Ala Val
1               5                   10

<210> SEQ ID NO 14
<211> LENGTH: 12
<212> TYPE: PRT
```

```
-continued

<213> ORGANISM: Artificial Sequence
<220> FEATURE:
<223> OTHER INFORMATION: ADA protein epitope

<400> SEQUENCE: 14

His Thr Leu Glu Asp Gln Ala Leu Tyr Asn Arg Leu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: ADA protein epitope

<400> SEQUENCE: 15

Leu Leu Pro Gly His Val Gln Ala Tyr Gln Glu Ala
1               5                   10

<210> SEQ ID NO 16
<211> LENGTH: 8
<212> TYPE: PRT
<213> ORGANISM: Artificial Sequence
<220> FEATURE:
<223> OTHER INFORMATION: ADA protein epitope

<400> SEQUENCE: 16

His Phe Gln His His His His His
1               5
```

WHOLE PROTEOME TILING MICROARRAYS

CROSS-REFERENCE TO RELATED APPLICATIONS

The present application claims the benefit of U.S. Provisional Application 61/454,214, filed Mar. 18, 2011, which is incorporated herein by reference in its entirety.

FIELD OF THE INVENTION

The present invention relates to a microarray comprising at least 50,000 oligopeptide features per $cm^2$ where the oligopeptide features represent at least 50%, at least 60%, at least 70%, at least 80%, at least 90%, at least 95%, at least 99%, or 100% of the proteome of a virus or an organism. The present invention further relates to methods for the synthesis of such microarrays and methods of using microarrays comprising at least 50,000 oligopeptide features per $cm^2$. In an embodiment of the invention, the oligopeptide features represent proteins expressed in the same species, wherein the oligopeptide features are presented in a tiling pattern representing at least about 5,000, at least about 10,000, at least about 15,000, at least about 20,000, or at least about 25,000 of the proteins expressed in a species. In some embodiments, the oligopeptide microarray features represent proteins expressed in the same species, wherein the microarray features are present in a tiling pattern that represents between about 5,000 and 50,000 of the proteins expressed in a species, between about 10,000 and 50,000 of the proteins expressed in a species, between about 15,000 and 50,000 of the proteins expressed in a species, between about 20,000 and 50,000 of the proteins expressed in a species, or between about 25,000 and 50,000 of the proteins expressed in a species.

BACKGROUND OF THE INVENTION

Oligopeptide microarrays are widely used in research and healthcare. Within these areas, oligopeptide microarrays are suitable for many different applications. Oligopeptide microarrays for example provide a tool for the identification of biologically active motifs, e.g. oligopeptide microarrays may imitate potential active motifs of ligands for screening the binding to corresponding receptors. Furthermore, the oligopeptide microarrays might reflect specific sequences of disease associated antigens. Such oligopeptide microarrays can be utilized to detect antibodies from patient samples suggesting the presence of certain inflammatory diseases, infections, and the like. Another important application of the oligopeptide microarrays is the discovery of biochemical interactions, including the binding of proteins or DNA. Oligopeptide microarrays can further be used for the profiling of cellular activity, the activity of enzymes, the adhesion of cells, and the like.

Traditional methods for the analysis of autoimmune diseases involves the detection of autoantibodies and include enzyme linked immunosorbent assays (ELISAs), Western blot analysis, immunoprecipitation analysis and flow-based assays. Routine assays for detection of autoantibodies is generally performed by ELISAs and fluorescence assays. Individual assays are performed in microtiter plates, with a single antigen per well. These tests are performed one-at-a-time, are laborious, and expensive. Oligopeptide arrays have been used to characterize and detect autoantibodies, but they have generally utilized purified antigen molecules spotted onto substrates. The antigens must be produced in recombinant expression systems and purified, which is a time-consuming process. These antigens are generally whole proteins, or known antigenic domains, and do not allow the characterization of specific epitopes. Synthetic peptide arrays have been utilized as well, however the production of these peptides is done by commercial automated peptide synthesizers, and then spotted onto slides. However, they cannot achieve the scale of peptides synthesized by maskless array synthesis (MAS) technology.

Traditional methods, such as ELISA, are laborious and costly, and can only be done one antigen at a time. While spotted oligopeptide microarrays are available, and allow parallel detection of multiple autoantibodies, the cost of producing those arrays is very expensive due to the cost of producing purified antigen molecules in a recombinant expression system. In addition they have a very low resolution and cannot achieve the comprehensive coverage of substantially the whole proteome that an oligopeptide microarray can. Many proteins cannot be synthesized in in vitro systems, which would prevent their use on such arrays.

Furthermore, antigens that are expressed and then spotted onto a microarray often only represent a small percentage of the full protein sequence. Antibodies in one patient may target one set of antigenic domains, which in another patient, the antibodies may target a completely different set of antigenic domains in the same protein. Such patient-to-patient differences could arise from misfolding of proteins, a common problem in autoimmune disease, thus causing differential presentation of protein domains to antibody producing B cells. Oligopeptide arrays are thus preferred because they allow all possible antigenic sites within a given protein to be examined in order to detect patterns or fingerprints across many patients.

The object of the present invention is the provision of microarrays with a high density oligopeptides with improved capabilities for high resolution analysis (including, but not limited to, serological analysis), a method for their synthesis and their use. The advantage of the microarrays according to the invention is their oligopeptide density and the coverage of substantially the whole proteome of an organism by the application of a tiling concept. Because of this oligopeptide density, the microarrays according to the invention allow the parallel detection of all autoantibodies in a human serum sample with a single binding assay. In addition, specific information about the location of epitopes is obtained from the assay by the introduction of the tiling concept. Therefore, the present invention provides a simple, cost-effective method for screening for a wide variety of autoimmune diseases, as well as rapid custom epitope mapping, screening peptides for small molecule binding, synthesis of antibody-like arrays for protein expression analysis, proteome-scale peptide scanning, and many more applications.

SUMMARY OF THE INVENTION

The present invention relates to a microarray with high density of oligopeptide features, thereby allowing for the detection of protein interactions across an organism's proteome. An embodiment of the invention is a microarray comprising at least 50,000 oligopeptide features per $cm^2$. Another embodiment is a microarray having oligopeptide features representing at least 50%, at least 60%, at least 70%, at least 80%, at least 90%, at least 95%, at least 99%, or 100% of the proteome of a target selected from a virus or organism.

BRIEF DESCRIPTION OF THE DRAWINGS

FIG. 2 depicts a representative "tiling" of poly(A) polymerase alpha (PAPOLA) sequence from amino acid 620 to amino acid 649 (SEQ ID NO:1).

FIG. 4 shows a summary of autoantibodies and epitopes determined through binding experiments.

FIG. 5 demonstrates a sensitivity titration of anti-PAPOLA antibody dilution.

FIG. 8 demonstrates binding of monoclonal anti-poly-Histidine on a full proteome array.

DETAILED DESCRIPTION OF THE INVENTION

Figure 1:
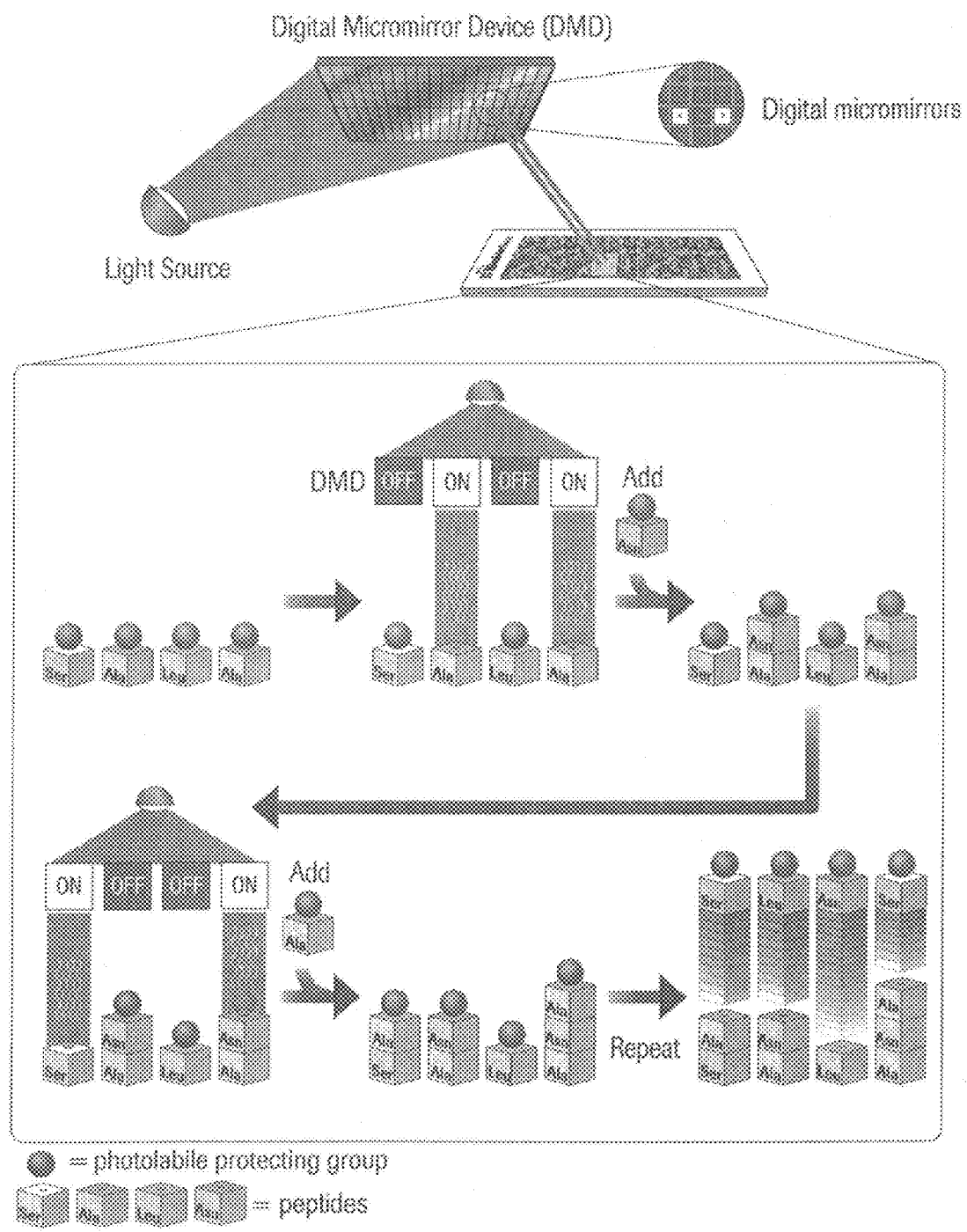
FIG. 1 depicts a synthetic process useful in the present invention, wherein a digital micromirror device is utilized for maskless array synthesis of oligopeptide arrays.

The following definitions are set forth to illustrate and define the meaning and scope of various terms used to describe the invention herein.

The term "microarray" as used herein refers to a two dimensional arrangement of features on the surface of a solid or semi-solid support. Features as used herein are defined areas on the microarray comprising biomolecules, such as peptides, nucleic acids, carbohydrates, and the like. The features can be designed in any shape, but preferably the features are designed as squares or rectangles. The features can exhibit any density of biomolecules. In some cases, the density is at least 10,000 features per cm$^2$.

The term "proteome" as used herein refers to all proteins or a set of proteins expressed by a genome, cell, tissue, or organism, including all proteins as contained in currently existing databases describing the expressed proteins of a particular organism, and further includes all variants or a set of variants of proteins resulting from alternative splicing of genes, all post-translationally modified proteins, and proteins translated from genes containing one or more single nucleotide polymorphisms (SNPs), frame shift mutations, deletions, inversions, and the like. Examples of existing databases describing the expressed proteins of various organisms are:

UniProt (Universal Protein Resource; uniprot.org on the World Wide Web);

Ensembl (ensembl.org on the World Wide Web);

VEGA (Vertebrate Genome Annotation; vega.sanger.ac.uk/ on the World Wide Web);

CCDS (Consensus CDS; ncbi.nlm.nih.gov/projects/CCDS/ on the World Wide Web);

UCSC Genome Browser (genome.ucsc.edu on the World Wide Web);

Protein database at NCBI (ncbi.nlm.nih.gov/protein on the World Wide Web); and

RCSB Protein Data Bank (pdb.org/ on the World Wide Web).

Such databases can be queried regarding particular organisms. For example, the UniProt database can be queried for proteins by taxonomy. For determination of proteins containing SNPs, one of skill in the art would look to currently existing databases containing information regarding SNPs, such as NCBI's dbSNP (ncbi.nlm.nih.gov/projects/SNP/ on the World Wide Web).

The term "posttranslational modification" as used herein refers to a chemical modification of a protein, the modification occurs after the translation of the protein. Posttranslational modifications include but are not limited to glycosylation, phosphorylation, acetylation, methylation, palmitoylation, amidation, and the like.

The term "serological response" as used herein refers to the production of antibodies within an organism, for example, within the human body, wherein the antibodies are directed against certain antigens. The antibodies can be directed against foreign antigens, such as molecules or structures on the surface of intruded molecules, compounds or microorganism. Preferably, the antibodies can be directed against the organism's own antigens (in instances of autoimmune diseases, precancerous lesions or cancer). Preferably, the organism's own antigens are proteins. The serological response can be measured by diagnostic tests, detecting the antibodies specific for the response in body fluids, preferably in serum, thereby giving information about the reason of the response in order to institute therapeutic actions. As diagnostic tests, test can be used known by the skilled person, such as ELISA, Western Blot, Agglutination, and the like.

The term "external stimulus" as used herein refers to stimuli inducing a serological response, whereas the stimuli have their origin outside the organism, preferably, the human body. External stimuli include but are not limited to microorganisms, pollen, peptides, proteins, poisons, and the like.

The term "autoimmune reaction" as used herein refers to malfunctions of the immune system, preferably the human immune system. Such malfunctions are characterized by the production of autoantibodies directed against the organism's own antigens or by the production of immune cells that target and attack particular cells or tissues of the body, preferably the human body. The autoimmune reaction can result in symptoms constituting an autoimmune disorder. The definition of autoimmune reaction includes, but is not limited to, immune reactions that occur in reaction to the presence of preneoplastic lesions, neoplastic lesions, malignant cells, malignant tissues.

The term "solid support" as used herein refers to any solid material, having a surface area to which organic molecules can be attached through bond formation or absorbed through electronic or static interactions such as covalent bond or complex formation through a specific functional group. The support can be a combination of materials such as plastic on glass, carbon on glass, and the like. The functional surface can be simple organic molecules but can also comprise of co-polymers, dendrimers, molecular brushes and the like.

The term "plastic" as used herein refers to synthetic materials, such as homo- or hetero-co-polymers of organic building blocks (monomer) with a functionalized surface such that organic molecules can be attached through covalent bond formation or absorbed through electronic or static interactions such as through bond formation through a functional group. Preferably the term "plastic" refers to polyolefin, which is a polymer derived by polymerization of an olefin (e.g., ethylene propylene diene monomer polymer, polyisobutylene). Most preferably, the plastic is a polyolefin with defined optical properties, like TOPAS® or ZEONOR/EX®.

The term "light transmission" as used herein refers to the property of matter, whereby the matter is transparent to a certain extent such that light can pass through the matter. The amount of light passing through is dependent on the extent of transparency or transmittance.

The term "spatially resolved photoirradiation" as used herein refers to the fact that light is directed precisely onto defined areas of a surface, preferably the surface of a microarray, by a device, such as an array of individually addressable aluminum micro mirrors. The device controls the overall pattern of light projected on the surface, thereby preparing the areas for the next coupling reaction. Preferably, light exposure leads to the cleavage of photolabile protecting groups and the un-masking of functional groups within the areas where the next component, e.g., an amino acid or a nucleotide, is to be coupled. This system is in parallel combined with a synthesizer in order to produce microarrays. By using this technique, that is directing light to individually addressable aluminum micro mirrors, 385,000 to 4.2 million unique probe features can be synthesized on a single microarray of microscope-slide size of 75×25 mm.

The term "maskless photolithography" as used herein refers to a technique for the synthesis of DNA or oligopeptide microarrays without the use of photo-masks. In maskless photolithography a device is used for directing light onto a defined area of a surface, preferably the surface of a microarray, in order to induce photo reactions, preferably the release of photolabile protecting groups. Examples for such a device can be a micro mirror device, a light-transmissive LCD display or a beam splitter. Preferably, the device is an array of individually addressable aluminum mirror elements that are operable under software control. Such mirror elements individually direct light onto a defined area of a surface, preferably the surface of a microarray. A preferred micro mirror device is the Digital Light Processor (DLP) from Texas Instruments, Inc.

The term "protecting group" as used herein refers to a substituent, functional group, ligand, or the like, which is cleavable bound (e.g., via covalent bond, ionic bond, or complex) to a potentially reactive functional group and prevents the potentially reactive functional group from reacting in an uncontrolled manner. Preferably, the protecting group is cleavable bound via a covalent bond. The protecting group can be cleaved off the respective reactive functional group by any fashion, such as by acids, bases, fluoride, enzymes, reduction or oxidation. Preferably, the protecting group is cleaved off by light exposure. Protecting groups according to the invention are photo labile protecting groups, which include, but are not limited to, o-nitrobenzyl-oxycarbonyl (NBOC), o-nitrophenyl-ethoxycarbonyl (NPEOC), 2-(3,4-methylenedioxy-2-nitrophenyl)-propyloxy-carbonyl (MeNPPOC), 2-(3,4-methylenedioxy-2-nitrophenyl)-oxycarbonyl (MeNPOC), 2-(2-nitrophenyl)-propoxycarbonyl (NPPOC), 2-(2-nitro-4-benzoylphenyl)-2'-propyl-1'-oxycarbonyl (Benzoyl-NPPOC), dimethoxy-benzo-inylyl-oxycarbonyl (DMBOC), 2-(2-nitrophenyl)-ethylsulfonyl (NPES), (2-nitrophenyl)-propylsulfonyl (NPPS), and the like.

The term "functional group" as used herein refers to any of numerous combinations of atoms that form parts of chemical molecules, that undergo characteristic reactions themselves, and that influence the reactivity of the remainder of the molecule. Typical functional groups are hydroxyl, carboxyl, aldehyde, carbonyl, amino, azide, alkynyl, thiol and nitril. Potentially reactive functional groups include, for example, amines, carboxylic acids, alcohols, double bonds, and the like. Preferred functional groups are potentially reactive functional groups of amino acids such as amino groups or carboxyl groups.

The term "natural amino acid" as used herein refers to one of the 20 amino acids used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine and lysine.

The term "non-natural amino acid" as used herein refers to an organic compound that is not among those encoded by the standard genetic code, or incorporated into proteins during translation. Therefore, non-natural amino acids include amino acids or analogs of amino acids, but are not limited to, the D-isostereomers of amino acids, the beta-amino-analogs of amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

The term "peptide" or "oligopeptide" as used herein refers to organic compounds composed of amino acids, which are arranged in a linear chain and joined together by peptide bonds between the carboxyl and amino groups of adjacent amino acid residues. The term "peptide" or "oligopeptide" preferably refers to organic compounds composed of less than 70 amino acid residues, more preferably of less than 35 amino acid residues, more preferably of less than 25 amino acid residues.

The term "amino group" as used herein refers to primary ($—NH_2$), or secondary ($—NHR_1$) amino groups. Examples of amino groups include, but are not limited to, $—NH_2$, $—NHCH_3$, $—NHC(CH_3)_2$. Examples of cyclic amino groups include, but are not limited to, aziridino, azetidino, pyrrolidino, piperidino, piperazino, morpholino, and thiomorpholino.

The term "reactive amino group" as used herein refers to an amine that can react with a functional group to form a covalent bond between the nitrogen of the amino group and the electrophile of the functional group, such as a peptide bond.

The term "polar organic solvent" as used herein refers to solvents which are water soluble in that a homogeneous mixture of the solvent in water is possible at room temperature under ambient conditions. Preferred polar organic solvents are methanol, ethanol, propanol, methyl ethyl ketone, acetonitrile, acetone, tetrahydrofuran (THF), dioxane, dimethylsulfoxide (DMSO), n-methyl-2-pyrrolidone (NMP), dimethylformamide (DMF), dimethylacetamide (DMA).

The term "base" as used herein refers to a substance capable of accepting a proton in polar or non-polar solvents. The base of choice for a particular reaction depends on the starting materials, the solvent and the temperature used for a specific reaction. Examples of bases include carbonate salts, phosphates, halides, hydroxides, hydrides, heterocyclic amines, disilylamides, trialkylamines, bicyclic amines, alkali metal hydrides, nitrogen-containing bases.

The term "synthesis cycle" as used herein refers to a predetermined number of successive reaction steps which are conducted to perform a synthesis of oligopeptides. Preferably the term "synthesis cycle" refers to a predetermined number of successive reaction steps which are conducted during solid phase synthesis of oligopeptides in order to attach the respective next amino acid to the previous functional group. Oligopeptide synthesis comprises a predetermined number of synthesis cycles, wherein in each cycle one specific amino acid is attached to the previous functional group. Therefore, the number of the cycles depends on the number of amino acids of the oligopeptide. For example, for the synthesis of a peptide micro array containing 20 amino acid building blocks, 20 cycles are required to elongate each feature of the peptide microarray by one amino acid residue. The combination of amino acid residues within an oligopeptide depends on the specific amino acids which are attached one after another to the respective previous functional group during the successive synthesis cycles.

The term "scavenger molecule" as used herein refers to an agent reactive with free radicals. Also, a scavenger molecule can be a molecule that reacts with olefins by means of an addition reaction as known in the field of peptide chemistry. Scavenger molecule according to the invention is an agent, which can be contained in polar organic solvents in order to react with side products of the deprotection step. Scavenger molecules include but are not limited to strong nucleophilic amines like piperidine, piperazine, imidazole and the like as well as radical quenchers, such as hydroxylamine, TEMPO, Oxo-TEMPO, sterically hindered phenols, and thiophenols.

Oligopeptide arrays of the present invention provide a number of uses not currently available with respect to existing oligopeptide array technology. As an example, such oligopeptide microarrays are useful in antibody detection related to autoimmune diseases. In general, autoimmune diseases result from an overactive immune response of the body to its own tissues and/or substances. The body attacks its own cells, resulting in various disease symptoms. More than 80 different autoimmune diseases are known. The symptoms of the different autoimmune diseases vary depending on the disease itself as well as the constitution of the patient's immune system. Some symptoms, however, might be identical between different autoimmune diseases. Symptoms include but are not limited to: fatigue, malaise, dizziness, high body temperature or fever, increased sensitivity to temperature in hands and feet. Severe symptoms are inflammation, weakness and stiffness of muscles and joints, digestive or gastrointestinal problems resulting in weight changes, blood sugar changes, abnormal blood pressure, irritability, anxiety or depression, reduced libido, infertility and change in size of an organ or even the destruction of an organ or tissue. The diversity of the symptoms and the difficult classification impedes effective diagnosis and therapeutic approaches. The success of a therapy of autoimmune diseases generally depend on an individual's symptoms, results from physical examination and diagnostic tests, the latter being an essential element of effective therapeutic approaches. Therefore simple, cost-effective methods of screening for a wide variety of autoimmune diseases are required.

Furthermore, oligopeptide microarrays are suitable for the analysis of basically any other disease involving interactions of proteins, which can be represented on an array. For example, oligopeptide microarrays provide a tool for the identification of biologically active motifs involved in the onset of certain diseases, e.g., oligopeptide microarrays may imitate potential active motifs of ligands for screening the binding to corresponding receptors. Furthermore, the oligopeptide microarrays might reflect specific sequences of disease associated antigens. Such oligopeptide microarrays can be utilized to detect antibodies from patient samples suggesting the presence of certain inflammatory diseases, infections, and the like. Another important application of the oligopeptide microarrays is the discovery of biochemical interactions, including DNA-protein-or protein-protein-interactions. Oligopeptide microarrays can further be used for the profiling of cellular activity, the activity of enzymes, the adhesion of cells, and the like.

Autoimmune applications are just one example of the utility of high-density oligopeptide arrays. Other applications include, but are not limited to, rapid custom epitope mapping, screening peptides for small molecule binding, synthesis of antibody-like arrays for protein expression analysis, proteome-scale peptide scanning, and many more applications.

Different methods for the production of oligopeptide microarrays can be used in the present invention. Spotting prefabricated peptides or in-situ synthesis by spotting reagents, e.g., on membranes, are two potential approaches. One of the most commonly used methods to generate peptide arrays of higher density are the so-called photolithographic techniques, where the synthetic design of the desired biopolymers is controlled by suitable photolabile protecting groups (PLPG) releasing the linkage site for the respective next component (amino acid, oligonucleotide) upon exposure to electromagnetic radiation, preferably light (Fodor et al., *Nature* 364 (1993) 555-556, Fodor et al., *Science* 251(1991) 767-773).

Two different photolithographic techniques are: 1) A photolithographic mask is used to direct light to specific areas of the synthesis surface effecting localized deprotection of the PLPG. The drawback of this technique is that a large number of masking steps are required resulting in a relatively low overall yield and high costs, e.g., the synthesis of a peptide of only six amino acids in length could require over 100 masks. 2) The second technique is the so-called maskless photolithography, where light is directed to specific areas of the synthesis surface effecting localized deprotection of the PLPG by digital projection technologies, such as micro mirror devices (Singh-Gasson et al., *Nature Biotechn.* 17 (1999) 974-978). Thus, time consuming and expensive production of exposure masks is unnecessary.

Synthesis cycle steps useful for the manufacture of oligopeptide microarrays of the present invention are exemplified in FIG. 1. In one embodiment, plastic solid supports comprising reactive amino groups and/or reactive ε-amino-hexanoic-acid linker moieties are irradiated using light from a light source directed to a digital micromirror device (DMD) which redirects the light onto the surface of the solid support. The illumination of a particular location using the DMD is either "on" or "off," depending upon whether a particular feature site should incorporate the next amino acid in the synthesis cycle. If the oligopeptide desired at a particular location requires such next successive amino acid, light reflected from the DMD at that particular location will be "on" (i.e., that particular feature will be illuminated), thus cleaving the protecting group from the amino acid present at that site. If the oligopeptide desired at a particular location should not incorporate the next successive amino acid, the DMD will be "off" in that position (i.e., that feature will not be illuminated), and the amino acid present at that site will remain protected.

In FIG. 1, four particular microarray features (features 1, 2, 3, and 4, respectively) are exemplified. Each feature is occupied by a protected amino acid from a previous synthesis cycle step. Features 2 and 4 are illuminated by the DMD, cleaving the protecting group from the respective amino acids at those features. The next successive amino acid, asparagine with a photolabile protecting group in this example, is then allowed to flow over the microarray and will incorporate into the activated features 2 and 4, but will not incorporate into the blocked features 1 and 3. Thus, the oligopeptides being constructed on features 2 and 4 are elongated by the addition of blocked asparagine, while the oligopeptides being constructed at features 1 and 3 remain unchanged. In the next synthesis cycle step as exemplified in FIG. 1, features 1 and 4 are illuminated by the DMD, cleaving the protecting group from the respective amino acids at those features, while features 2 and 3 remain protected. Protected alanine is then allowed to flow over the microarray, and incorporates into features 1 and 4 but does not incorporate into features 2 and 3. Successive steps continue until the appropriate oligopeptides are synthesized at all four features.

In certain methods, amino acids introduced in the synthesis of oligopeptide microarrays are protected with NPPOC or MeNPOC, respectively. The method using NPPOC protected amino acids has the disadvantage that the half-life of all (except one) protected amino acids is within the range of approximately 2 to 3 minutes under certain conditions. In contrast, under the same conditions, NPPOC-protected tyrosine exhibits a half-life of almost 10 minutes. As the velocity of the whole synthesis process depends on the slowest sub-process, this phenomenon increases the time of the synthesis process by a factor of 3 to 4. Concomitantly, the degree of damage by photogenerated radical ions to the growing oligomers increases with increasing and excessive light dose requirement. Amino acids, which are protected with Benzoyl-NPPOC, show a half-life of approximately 2 to 3 minutes, including Benzoyl-NPPOC-protected tyrosine. The drawback of using exclusively Benzoyl-NPPOC-protected amino acids is that the dissociated protecting groups adhere to the solid support, thereby inhibiting the synthesis process of the oligopeptides, a phenomenon that is unknown for DNA arrays and is being attributed to light induced addition of the released benzophenone moiety to either the growing peptide chain or the solid support itself. In protein array technology, plastic derived supports are preferred due to their low non-specific binding to proteins samples. However, benzophenone moieties are well known in the state of the art to add to hydrocarbons as present in plastic surfaces by a radical mechanism.

In one aspect of the invention, the oligopeptides of each feature can have a length of between 9 and 18 amino acid residues. In some cases, the oligopeptide features are between 10 and 15 amino acids in length. In another embodiment, the length of the oligopeptides is 12 amino acid residues. In one embodiment, substantially all of the oligopeptide features are the same length. For example, at least 90%, at least 95%, at least 99%, or 100% of the oligopeptide features can be the same length in a microarray provided herein. In some cases, the sequences of the oligopeptide features of a microarray provided herein are substantially identical. In a further aspect of the invention, the amino acid sequence of each feature overlaps the amino acid sequence of at least one other feature by at least 3, at least 6, or at least 9 contiguous amino acid residues. In one embodiment, the sequence of each feature has an overlap of n−1 with at least one other feature, wherein n=the length of the oligopeptide of the at least one other feature.

In one aspect of the invention, each oligopeptide feature represents a portion of a target proteome, where the target is selected from a virus and an organism. Organisms appropriate for the microarrays and methods provided herein can include mammalian species (e.g., human, mouse), plant species (e.g., *Arabidopsis*), insect species (e.g., *Drosophila*), prokaryotes, yeast, and fungi.

In an embodiment of the invention, the oligopeptide features represent proteins expressed in the same species, wherein the oligopeptide features are presented in a tiling pattern representing at least 5,000 of the proteins expressed in a species, at least 10,000 expressed proteins, at least 15,000 expressed proteins, at least 20,000 expressed proteins, or at least 25,000 expressed proteins. In some embodiments, the oligopeptide features represent proteins expressed in the same species, wherein the oligopeptide features are present in a tiling pattern that represents between about 5,000 and 50,000 expressed proteins, between about 10,000 and 50,000 expressed proteins, between about 15,000 and 50,000 expressed proteins, between about 20,000 and 50,000 expressed proteins, or between about 25,000 and 50,000 expressed proteins.

In another aspect of the invention, the oligopeptide features represent proteins expressed in a mammalian proteome, wherein the oligopeptide features are present in a tiling pattern that represents at least 5,000 mammalian proteins, at least 10,000 mammalian proteins, at least 15,000 mammalian proteins, or at least 20,000 mammalian proteins. In some embodiments, the oligopeptide features represent proteins expressed in a mammal, wherein the oligopeptide features are present in a tiling pattern that represents between about 5,000 and 50,000 mammalian proteins, between about 10,000 and 50,000 mammalian proteins, between about 15,000 and 50,000 mammalian proteins, between about 20,000 and 50,000 mammalian proteins, or between about 25,000 and 50,000 mammalian proteins.

In another aspect of the invention, the oligopeptide features represent proteins expressed in the human proteome, wherein the oligopeptide features are present in a tiling pattern that represents at least 5,000 human proteins, at least 10,000 human proteins, at least 15,000 human proteins, or at least 20,000 human proteins. In some embodiments, the oligopeptide features represent proteins expressed in human, wherein the oligopeptide features are present in a tiling pattern that represents between about 5,000 and 50,000 human proteins, between about 10,000 and 50,000 human proteins, between about 15,000 and 50,000 human proteins, between about 20,000 and 50,000 human proteins, or between about 25,000 and 50,000 human proteins.

In another aspect of the invention, the oligopeptide features represent proteins expressed in the mouse proteome, wherein the oligopeptide features are present in a tiling pattern that represents at least 5,000 mouse proteins, at least 10,000 mouse proteins, at least 15,000 mouse proteins, or at least 20,000 mouse proteins. In some embodiments, the oligopeptide features represent proteins expressed in mouse, wherein the oligopeptide features are present in a tiling pattern that represents between about 5,000 and 50,000 mouse proteins, between about 10,000 and 50,000 mouse proteins, between about 15,000 and 50,000 mouse proteins, between about 20,000 and 50,000 mouse proteins, or between about 25,000 and 50,000 mouse proteins.

In another embodiment, the oligopeptide features represent proteins expressed in a plant proteome, wherein the oligopeptide features are present in a tiling pattern that represents at least 5000 plant proteins, at least 10,000 plant proteins, at least 15,000 plant proteins, at least 20,000 plant proteins, or at least 25,000 plant proteins. In some embodiments, the oligopeptide microarray features represent proteins expressed in plant, wherein the oligopeptide features are present in a tiling pattern that represents between about 5,000 and 50,000 plant proteins, between about 10,000 and 50,000 plant proteins, between about 15,000 and 50,000 plant proteins, between about 20,000 and 50,000 plant proteins, or between about 25,000 and 50,000 plant proteins.

In another embodiment, the oligopeptide features represent proteins expressed in the *Arabidopsis* proteome, wherein the oligopeptide features are present in a tiling pattern that represents at least about 5,000 *Arabidopsis* proteins, at least 10,000 *Arabidopsis* proteins, at least 15,000 *Arabidopsis* proteins, at least 20,000 *Arabidopsis* proteins, or at least 25,000 *Arabidopsis* proteins. In some embodiments, the oligopeptide features represent proteins expressed in *Arabidopsis*, wherein the oligopeptide features are present in a tiling pattern that represents between about 5,000 and 50,000 *Arabidopsis* proteins, between about 10,000 and 50,000 *Arabidopsis* proteins, between about 15,000 and 50,000 *Arabidopsis* proteins, between about 20,000 and 50,000 *Arabidopsis* proteins, or between about 25,000 and 50,000 *Arabidopsis* proteins.

In another embodiment, the oligopeptide features represent proteins expressed in an insect proteome, wherein the oligopeptide features are present in a tiling pattern that represents at least 5,000 insect proteins, at least 10,000 insect proteins, or at least about 15,000 insect proteins. In some embodiments, the oligopeptide features represent proteins expressed in insect, wherein the oligopeptide features are present in a tiling pattern that represents between about 5,000 and 30,000 insect proteins, between about 10,000 and 30,000 insect proteins, between about 15,000 and 30,000 insect proteins, between about 20,000 and 30,000 insect proteins, or between about 25,000 and 30,000 insect proteins.

In another embodiment, the oligopeptide features represent proteins expressed in the *Drosophila* proteome, wherein the oligopeptide microarray features are present in a tiling pattern that represents at least 5000 *Drosophila* proteins, at least 10,000 *Drosophila* proteins, or at least about 15,000 *Drosophila* proteins. In some embodiments, the oligopeptide microarray features represent proteins expressed in *Drosophila*, wherein the oligopeptide features are present in a tiling pattern that represents 5,000 to 50,000 *Drosophila* proteins, 10,000 to 50,000 *Drosophila* proteins, 15,000 to 50,000 *Drosophila* proteins, 20,000 to 50,000 *Drosophila* proteins, or 25,000 to 50,000 *Drosophila* proteins.

In another aspect of the invention, the oligopeptide features represent proteins expressed in prokaryotes, wherein the oligopeptide features are present in a tiling pattern that represents at least 2000 prokaryote proteins, at least 3,000 prokaryote proteins, at least 4,000 prokaryote proteins, or at least 5,000 prokaryote proteins. In some embodiments, the oligopeptide features represent proteins expressed in prokaryotes, wherein the oligopeptide features are present in a tiling pattern that represents between about 2,000 and 10,000 prokaryote proteins, between about 3,000 and 10,000 prokaryote proteins, between about 4,000 and 10,000 prokaryote proteins, or between about 5,000 and 10,000 prokaryote proteins.

In another aspect of the invention, the oligopeptide features represent proteins expressed in *E. coli*, wherein the oligopeptide features are present in a tiling pattern that represents at least 2000 *E. coli* proteins, at least 3,000 *E. coli* proteins, at least 4,000 *E. coli* proteins, or at least 5,000 *E. coli* proteins. In some embodiments, the oligopeptide features represent proteins expressed in *E. coli*, wherein the oligopeptide features are present in a tiling pattern that represents between about 2,000 and 10,000 *E. coli* proteins, between about 3,000 and 10,000 *E. coli* proteins, between about 4,000 and 10,000 *E. coli* proteins, or between about 5,000 and 10,000 *E. coli* proteins.

In another aspect of the invention, the oligopeptide features represent proteins expressed in fungi, wherein the oligopeptide features are present in a tiling pattern that represents at least 2000 fungi proteins, at least 3,000 fungi proteins, at least 4,000 fungi proteins, or at least 5,000 fungi proteins. In some embodiments, the oligopeptide features represent proteins expressed in fungi, wherein the oligopeptide features are present in a tiling pattern that represents between about 2,000 to 10,000 fungi proteins, between about 3,000 to 10,000 fungi proteins, between about 4,000 to 10,000 fungi proteins, or between about 5,000 to 10,000 fungi proteins.

In another aspect of the invention, the oligopeptide features represent proteins expressed in yeast, wherein the oligopeptide features are present in a tiling pattern that represents at least 2000 yeast proteins, at least 3,000 yeast proteins, at least 4,000 yeast proteins, or at least 5,000 yeast proteins. In some embodiments, the oligopeptide features represent proteins expressed in yeast, wherein the oligopeptide features are present in a tiling pattern that represents between about 2,000 to 10,000 yeast proteins, between about 3,000 to 10,000 yeast proteins, between about 4,000 to 10,000 yeast proteins, or between about 5,000 to 10,000 yeast proteins.

The present invention also concerns a method for the synthesis of an oligopeptide microarray as described in the previous paragraphs. In several embodiments, the overlap of each oligopeptide feature with another feature is exactly 9 amino acids on microarrays produced according to the method of the invention.

The present invention further concerns the use of an oligopeptide microarray for serological analysis. In some cases, a microarray described herein is used for analysis of a serological response to an external stimulus. In another embodiment, a microarray described herein is used for detecting an autoimmune reaction.

One aspect of the present invention is an oligopeptide microarray comprising at least 50,000 features per $cm^2$, characterized in that the features represent at least 50%, at least 60%, at least 70%, at least 80%, at least 90%, at least 95%, at least 99%, or 100% of the proteome of a target proteome, where the target is selected from a virus or an organism. In one embodiment the microarray comprises oligopeptide features representing the human proteome, where the oligopeptide features represent at least 90%, at least 95%, at least 99%, or 100% of the human proteome.

Another aspect of the present invention are high density microarrays that have extensive features in a compact area. Embodiments of the present microarrays can have a variety of oligopeptide feature densities. For example, the microarrays of the present invention comprise at least 10,000 oligopeptide features/$cm^2$, 50,000 oligopeptide features/$cm^2$, at least 100,000 oligopeptide features/$cm^2$, at least 200,000 oligopeptide features/$cm^2$, at least 300,000 oligopeptide features/$cm^2$, at least 400,000 oligopeptide features/$cm^2$, at least 500,000 oligopeptide features/$cm^2$, or at least 1,000,000 oligopeptide features/$cm^2$. Further, certain embodiments of microarrays have feature density within a variety of feature density ranges. For example, the density can comprise a range of 10,000 to 1,000,000 oligopeptide features/$cm^2$, 50,000 to 1,000,000 oligopeptide features/$cm^2$, 100,000 to 1,000,000 oligopeptide features/$cm^2$, 200,000 to 1,000,000 oligopeptide features/$cm^2$, 300,000 to 1,000,000 oligopeptide features/$cm^2$, 400,000 to 1,000,000 oligopeptide features/$cm^2$, 500,000 to 1,000,000 oligopeptide features/$cm^2$, 10,000 to 500,000 oligopeptide features/$cm^2$, 50,0000 to 500,000 oligopeptide features/$cm^2$, 100,000 to 500,000 oligopeptide features/$cm^2$, 200,000 to 500,000 oligopeptide features/$cm^2$, or any range found within a lower level of 10,000 and an upper level of 1,000,000 oligopeptide features/$cm^2$.

In one embodiment, the microarray has a density of at least 10,000 oligopeptide features per $cm^2$ and, in some cases, at least 50,000 oligopeptide features per $cm^2$. Applied to the area of a microarray, a single microarray of 75×25 mm size may contain at least 385,000 unique oligopeptide features, at least 720,000 unique oligopeptide features, or at least 2.1 million unique oligopeptide features.

In another embodiment, oligopeptides of each feature can have basically any length on the array. In some cases, the oligopeptides have a length of between 2 and 50 amino acid residues. I some cases, the oligopeptides can have a length of between 5 and 25 amino acid residues or between 9 and 18 amino acid residues.

In another embodiment, substantially all of the oligopeptides are the same length. In some cases, substantially all of the oligopeptides are between 2 and 50 amino acid residues in length, between 5 and 25 amino acid residues in length, between 10 and 15 amino acid residues in length, and in certain embodiments, are 12 amino acid residues long.

In yet another embodiment, the sequence of each feature has an overlap of at least 3, at least 6, and or at least 9 contiguous amino acid residues with the amino acid sequence of at least one other feature. In one embodiment, the sequence of each feature has an overlap of n−1 with at least one other feature, wherein n=the length of the oligopeptide of the at least one other feature.

In the present invention, protein sequences representing either the entire proteome or specific autoimmune disease targets are tiled on the oligopeptide microarray according to the invention and an antibody binding assay performed using human sera. Fluorescently labeled secondary antibodies can then be bound to the oligopeptide microarray to detect which oligopeptides on the microarray the antibodies in the sera have bound. One of skill in the art will appreciate that other methods for detection of binding are also available, such as (but not limited to) direct labeling of the binding antibody. Direct labeling methods would be particularly suited when the present invention is used to investigate the binding of monoclonal antibodies. Further, it is understood that the present invention is not necessarily limited to antibodies, but can be applied to antibody fragments, or other binding partners that specifically target a protein or peptide.

Oligopeptides can be tiled for protein sequences in various ways, depending on the array platform and number of protein targets. As examples, for a full proteome design utilizing the 2.1M platform, 12-mer oligopeptides at a 3 amino acid step, or 16-mer peptides at a 6 amino acid step, can be used. The former would allow the characterization of all 9-mer epitopes in the proteome, and the latter would allow the characterization of all 10-mer epitopes.

For the present invention, the construction of the oligopeptide microarray involves the collection of the protein sequences representing the proteome of a virus or an organism, for example, the human proteome. Respective information is often publicly available. Peptides are produced from the protein sequences by grabbing substrings from the protein sequence. The substrings are 12 to 16 amino acids in length, and are selected at 3 to 6 amino acid spacing, illustrating the tiling concept of the present invention. A simple compression algorithm, identical to the one used for DNA synthesis is used to either discard, or truncate, peptide sequences that would take too long to produce. The peptide sequences are laid out in an array design using software, such as the ArrayScribe software, and mask files are produced for the 3P MAS unit using a custom perl script analogous to the method used to produce DNA array masks. Arrays are synthesized on a MAS unit, and processed in a manner identical to other peptide arrays. Binding can be done using mixers and following protocols known by the skilled person. Detection of the signal via fluorescently labeled secondary antibodies is done via methods known by the skilled person. Scanning and quantification of images can be accomplished using MS200 scanner and NimbleScan software.

FIG. 2 provides an example of the tiling concept utilized in certain embodiments of the present invention. The top line of FIGS. 2A-2C each show the PAPOLA protein sequence from amino acid 620 to amino acid 649 (the "PAPOLA sequence").

In FIG. 2A, a set of 4 probe features is illustrated beneath the PAPOLA sequence that embodies a set of 12-mer oligopeptides wherein the probes in each feature differs by one amino acid (a 1×12 array). Thus, a set of probe features configured as a 1×12 array will have an overlap of 11 amino acids between a particular feature and at least one other feature. One alternative tiling embodiment is illustrated in FIG. 2B. Again, the top line shows the PAPOLA sequence; however, the tiling arrangement of the 4 illustrated probe features is designed so that each feature has 12-mer probes that differ by 3 amino acids (a 3×12 array). Thus, a set of probe features configured as a 3×12 array will have an overlap of 9 amino acids between a particular feature and at least one other feature. In FIG. 2C, another embodiment is illustrated wherein the probe features are again 12-mers, but the "step" between features is 6 amino acids (a 6×12 array). In such an array, a set of probe features configured as a 6×12 array will have an overlap of 6 amino acids between a particular feature and at least one other feature.

Another aspect of the present invention is a method for the synthesis of an oligopeptide microarray as described above. In one embodiment, a method is used wherein the overlap of each feature in amino acid sequence with the amino acid sequence of another feature is between 2 and 40 amino acid residues, between 5 and 20 amino acids, between 8 and 15 amino acids, or, in some cases, exactly 9 amino acids.

In another aspect, the present invention provides methods for using oligopeptide microarrays. For example, microarrays of the present invention are useful in antibody detection related to autoimmune diseases. A microarray as described above can be used for any analysis of suitable tissue or body fluid, preferably for serological analysis. One embodiment is the use of an oligopeptide microarray as described above for the analysis of a serological response to internal or external stimuli, preferably external stimuli. Another embodiment is the use of an oligopeptide microarray as described above for detecting an autoimmune reaction. In some cases, an oligopeptide microarray can be used for characterization of the antigen binding capacity of an antisera, an antibody, or a fragment of an antibody. For example, a microarray can be used for characterization of the antigen binding capacity of a monoclonal antibody or a polyclonal antisera.

The NPPOC-protected amino acids were synthesized by adding the respective amino acid to a $Na_2CO_3$ solution in $H_2O$. To that solution tetrahydrofurane (THF) was added subsequently. Afterwards, a solution of 2-nitrophenyl-2-propan-1-ol (NPPOC—Cl) in THF was added. THF was removed in a rotary evaporator under vacuum and the residue was extracted. The residue was acidified and extracted with ethylacetate. Extracts were washed with $H_2O$ and evaporated in vacuo to dryness. The residue was dissolved in dichloromethane and purified by column chromatography.

The microarray according to the invention can be synthesized according to the following steps:
a) providing a plastic solid support
b) coupling to the plastic solid support an amino acid which is protected at its amino group with NPPOC or a derivative thereof
c) optionally capping unreacted amino acids
d) optionally washing the plastic solid support
e) deprotecting the amino acid by photoirradiation at 350 to 410 nm
f) repeating steps b) to e) for a predetermined number of times.

Alternatively, the microarray according to the invention can be synthesized according to the following steps:

a) providing a plastic solid support, the solid support having a primary or secondary amine coupled to the surface
b) coupling to the plastic solid support an amino acid which is protected at its amino group with NPPOC or a derivative thereof
c) optionally, capping sites that did not couple the amino acid derivative of the previous step
d) optionally washing the plastic solid support
e) site selectively deprotecting the amino acid by photoirradiation at 350 to 410 nm, the selection being provided by a mask or a mask-free device, preferably in a polar organic solvent, most preferably containing a scavenger molecule to react with side products of this deprotection step
f) repeating steps b) to e) for a predetermined number of times.

Alternatively, the microarray according to the invention can be synthesized according to the following steps:
a) providing a plastic solid support, the solid support having a primary or secondary amine coupled to the surface
b) coupling to the plastic solid support an amino acid which is protected at its amino group with NPPOC or a derivative thereof, forming a peptide bond to the solid support
c) optionally, capping sites that did not couple the amino acid derivative of the previous step
d) optionally, washing the solid support
e) site selectively deprotecting the amino acid by photoirradiation at 350 to 410 nm, that selection being provided by a mask or a mask-free device, preferably in a polar organic solvent, most preferably containing a scavenger molecule to react with side products of this deprotection step
f) repeating steps b) to e) for a predetermined number of times
g) deprotecting all "permanent protection groups" located at the side-chains of amino acids, e.g. Lysine(e-amino-BOC)—
h) optionally, treating the peptide microarray with a reducing agent in order to reverse oxidative damage occurring at Cysteine- or Methionine-sulfur.

The support of the microarray can be made of any material known by the skilled person used for the synthesis of a microarray, preferably the support is made of plastic, glass, carbon on glass, metal on glass, plastic on glass. Preferably, plastic is used as a support. Most preferred is a plastic solid support. More preferably, the support comprises a surface layer and a body, wherein the body consists of polyolefin. More preferred is that the surface of the support comprises reactive amino groups. More preferably, ε-amino-hexanoic-acid is coupled to the surface of the support. The support can be provided in any shape, such as beads, gels, plates, membranes, slides or preferably chips. The C-terminal amino acid residues can be bound to the surface of the support, preferably a plastic solid support, via peptide bonds. The C-terminal amino acids of the oligopeptides can be coupled to the surface of the support, preferably a plastic solid support, with ε-amino-hexanoic-acid.

The surface of the support can comprises functional groups, capable of forming bonds, such as peptide bonds. Preferably the surface of the support can be coated with a respective compound, which then provides the functional groups, capable of forming the bonds. The support can be coated with ε-amino-hexanoic-acid or ε-amino-hexanoic-acid, which is coupled to the surface of the support.

The first amino acid, which is coupled to the support and the following amino acids coupled thereto are protected by any protecting group capable of preventing the potentially reactive functional group of the amino acid from reacting under certain reaction conditions. Preferred protecting groups are o-nitro-benzyloxy-carbonyl (NBOC), o-nitrophenyl-ethoxycarbonyl (NPEOC), 2-(3,4-methylenedioxy-2-nitrophenyl)-propyloxy-carbonyl (MeNPPOC), 2-(3,4-methylenedioxy-2-nitrophenyl)-oxycarbonyl (MeNPOC), dimethoxy-benzo-inylyl-oxycarbonyl (DMBOC), 2-(2-nitrophenyl)-ethylsulfonyl (NPES) and (2-nitrophenyl)-propylsulfonyl (NPPS). Most preferred protecting groups are 2-(2-nitrophenyl)-propoxycarbonyl (NPPOC), or derivatives thereof. Preferably the used protecting groups are NPPOCs and/or NPPOC derivatives. Preferably, the derivatives are 2-(2-nitro-4-benzoyl-phenyl)-propoxycarbonyl (NPPOC), Benzoyl-NPPOCs.

Any natural or non-natural amino acid protected by the above mentioned protecting groups can be used for the synthesis of peptide microarrays. Preferably, natural amino acids are used for the synthesis of oligopeptide microarrays. The amino acids can be protected by NPPOCs and/or NPPOC derivatives, such as Benzoyl-NPPOC. 16-19 different amino acids, such as histidine, alanine, valine, glycine, leucine, isoleucine, aspartic acid, glutamic acid, serine, glutamine, asparagine, threonine, arginine, proline, phenylalanine, tryptophan, cysteine, tyrosine, methionine and lysine, which are protected with NPPOCs and/or NPPOC derivatives are used. Some amino acids can be protected with Benzoyl-NPPOC, preferably tyrosine is protected with Benzoyl-NPPOC.

Protecting groups are cleavable bound to potentially reactive functional groups of amino acids in order to prevent the potentially reactive functional groups from reacting in an uncontrolled manner. The protecting groups are preferably cleavable bound to the amino acids by a covalent binding. The protecting groups can be cleaved off the respective functional group by any fashion, such as by acids, bases, fluoride, enzymes, reduction or oxidation. Preferred is the use of photolabile protecting groups, which are cleaved off by light exposure or irradiation, respectively.

Irradiation can be used for cleaving off the photolabile protecting groups, which spans the whole spectrum of electromagnetic radiation. Preferred for cleaving off the photolabile protecting group is the range from UV- to the IR-light, ranging approximately from 200 nm to 700 nm. More preferred deprotection is performed at 200 nm to 400 nm. Deprotection can be performed at 350 to 410 nm. In some cases, deprotection can be performed at 350 to 375 nm. In other cases, deprotection can be performed at 360 to 370 nm or, in some cases, at around 365 nm.

The support can be non-transparent or transparent for light in the range from UV- to the IR-light. Preferably, the support has at least 50% light transmission, preferably 60% light transmission, and more preferably 75% light transmission in the range from UV- to the IR-light. The support can have at least 50%, at least 60%, and at least 75% light transmission at a wavelengths of 350 to 410 nm. In some cases, the support can have at least 50%, at least 60%, and at least 75% light transmission at wavelengths of 350 to 375 nm. In some cases, the support can have at least 50%, at least 60%, and at least 75% light transmission at wavelengths of 360 to 370 nm. In some cases, the support can have at least 50%, at least 60%, and at least 75% light transmission at wavelengths of about 365 nm.

The washing step of the support between the capping step and the deprotection step of the method for synthesis of an oligopeptide microarray can be optional. Preferably there are one or more washing steps between the capping step and the deprotection step of the method for synthesis of an oligopeptide microarray. Washing of the support is performed by a polar organic solvent or a mixture of organic solvents.

Synthesis of the oligopeptide microarrays can be performed using photolithography-based techniques. Therefore, a photolithographic mask is used to expose respective features to light in order to deprotect the functional groups, preferably the alpha-amino groups of the peptides, for coupling of the next amino acid. Preferably, maskless photolithography is used to direct light onto respective features on an oligopeptide microarray. For this purpose, maskless photolithography uses controllable devices, e.g., computer controlled devices, which have individually addressable elements to direct light onto respective features. Such controllable devices are selected from, but not limited to, light-transmissive LCD displays and beam splitters. Preferably, a digital micro mirror device is used as a controllable device, which is an array of individually addressable aluminum mirror elements that are operable under software control. Such elements redirect light onto respective features on a microarray. Most preferred as a micro mirror device is the Digital Light Processor (DLP) from Texas Instruments, Inc.

Photoirradiation can be spectrally limited to wavelengths of 350 to 410 nm, preferably to wavelengths of 350 to 375 nm, more preferably to wavelengths of 360 to 370 nm, much more preferably to wavelengths of 363 to 367 nm and most preferred wavelengths of 365 nm.

Spatial resolution by directing light onto respective features over individually addressable aluminum micro mirrors may lead to many densities of choice of oligopeptides per surface area. The microarray can have a density of at least 10,000 and preferably at least 50,000 oligopeptide features per cm$^2$. Applied to the area of a microarray, a single microarray of 75×25 mm size may contain at least 385,000 unique oligopeptide features, preferably at least 720,000 unique oligopeptide features, more preferably at least 2.1 million unique oligopeptide features.

The oligopeptides synthesized on the microarray can have any length and can contain any number of the same or of different amino acid residues. Preferably, the oligopeptides synthesized on the microarray have at least 35 amino acid residues, more preferably the oligopeptides synthesized on the microarray have at least 25 amino acid residues, preferred are oligopeptides synthesized on the microarray consisting of 6 to 24 amino acids and preferably 9 to 18 amino acids.

Photoirradiation can be performed in the presence of an organic solvent, preferably a polar organic solvent. In some cases, photoirradiation is performed in the presence of a polar organic solvent or a mixture of solvents, selected from a group consisting of, but not limited to, dimethylsulfoxide, n-methyl-2-pyrrolidone, dimethylformamide, acetonitrile, methanol, ethanol and propanol.

Deprotection, especially by photoirradiation, can be performed in the absence and in the presence of a base. Suitable bases include carbonate salts, ammonium salts, phosphates, thiolate salts, hydroxides, hydrides, heterocyclic amines, disilylamides, trialkylamines, bicyclic amines, organic acid salts and nitrogen-containing bases. The base in which photoirradiation is performed can be selected from either hydrazine, hydroxylamine or imidazole. Most preferred are weak basic, yet nucleophilic and weak reducing bases.

Methods used for the synthesis of oligopeptides or oligopeptide microarrays are designed in repeating cycles, comprising the basic steps of coupling, optionally capping, optionally washing and deprotecting. During each cycle another amino acid is coupled to the oligopeptide. Therefore, the number of cycles is determined by the length of the synthesized oligopeptides. Each step has a defined duration dependent on the velocity of the associated chemical reaction. One limiting factor concerning the synthesis of oligopeptides or oligopeptide microarrays is the deprotection step together with the coupling step. Cleaving off the protecting group by light exposure depends on the one hand on physical parameters, such as pH, temperature, salt content, light intensity and wavelengths. On the other hand cleaving off the protecting group by light exposure depends on, which amino acid is used in the respective cycle in conjunction with which protecting group. For example, the deprotection time of NPPOC-protected tyrosine is increased by a factor of 3 to 4 as compared to the remaining natural amino acids. Thus, NPPOC-protected tyrosine is the major time limiting factor of the synthesis of oligopeptides or oligopeptide microarrays. In contrast, the deprotection time of Benzoyl-NPPOC protected tyrosine is on the same level as the remaining natural amino acids protected with NPPOC. Thus, using Benzoyl-NPPOC protected tyrosine together with the remaining 19 natural amino acids protected with NPPOC leads to the removal of the major time limiting factor of the synthesis of oligopeptides or oligopeptide microarrays and thus to a significant increase in velocity. Coupling steps of each synthesis cycle can be less than 15 minutes, less than 10 minutes, or less than 5 minutes.

It is essential to have an active alignment of the microarray and the oligopeptide features, respectively, to the optical part between the synthesis cycles in order to ensure the light exposure solely on the respective features. Therefore, it is necessary to adjust the position of the oligopeptide microarray over a duration of over 36 hours accurately in one and the same position with a tolerance of about 1 μm. To achieve this goal, the oligopeptide array and the micro mirror array are both actively aligned by a control system. Positioning of photoirradiation beams onto the support can be controlled and adjusted over time. In some cases, positioning of photoirradiation beams onto the support can be controlled and adjusted before at least each 4$^{th}$ irradiation (deprotection step) or, in some cases, before each irradiation.

The support can be made of any material known by the skilled person used for the synthesis of an oligopeptide microarray, preferably the support is made of plastic, glass, carbon on glass, metal on glass, or plastic on glass. Preferably, plastic is used as a support. Most preferred is a plastic solid support. Adjustment can be performed by means of adjusting the position of the plastic solid support.

The microarray can be located on a support, preferably a plastic solid support, comprising at least 10,000 and preferably at least 50,000 oligopeptide features per cm$^2$. Applied to the area of a microarray, a single microarray may contain at least 385,000 unique oligopeptide features, preferably at least 720,000 unique oligopeptide features, more preferably at least 2.1 million unique oligopeptide features.

The C-terminal amino acid residues of the oligopeptide microarray are covalently bound to the surface of the support, preferably a plastic solid support, via peptide bonds. The C-terminal amino acids of the oligopeptides can also be coupled to the surface of the support, preferably a plastic solid support, with an ε-amino-hexanoic-acid linker moiety.

The following examples are provided to aid the understanding of the present invention, the true scope of which is set forth in the appended claims. It is understood that modifications can be made in the procedures set forth without departing from the spirit of the invention.

EXAMPLES

Example 1

Creation of CCDS Proteome Design

The collection of protein sequences was downloaded from the Consensus Coding Sequence (CCDS) database (available at ncbi.nlm.nih.gov/CCDS/CcdsBrowse.cgi on the World Wide Web; archive CCDSprotein.20090902.faa.gz). This set contained 23,754 protein sequences, totaling 13,405,531 amino acids (aa). A custom perl script was used to generate 12-mer oligopeptides from each protein sequence, at an interval of 6 aa. The number of synthesis cycles necessary to synthesize each oligopeptide was evaluated using the following amino acid sequence: A, R, N, D, C, E, Q, G, H, I, L, K, M, F, P, S, T, W, Y, V. Oligopeptides that could not synthesized using 7 repetitions of the preceding sequence were truncated to a minimum length of 8 aa. If they still could not be synthesized at that minimal length, the oligopeptide was discarded. For this set of protein sequences, 1,931 oligopeptides were discarded, mostly consisting of long runs of single amino acids. An additional 39 oligopeptides were discarded because they contained codes for non-standard amino acids. After discarding these 1,970 oligopeptides, a set of 2,198,610 oligopeptides remained. With these oligopeptide deletions, only 22 proteins were completely eliminated from the CCDS dataset.

Roche NimbleGen's array layout software, ArrayScribe, was used to randomly distribute the oligopeptides across the array design template. The final array design consisted of three 1050 feature wide×1400 feature high subarrays. Each feature was 13.67 µm square. The oligopeptides were arranged randomly in a checkerboard fashion in each subarray, such that a maximum of 735000 oligopeptides could be synthesized on each subarray. After placement of the oligopeptides, a series of files was produced to direct the light-mediated deprotection of individual features for each amino acid synthesis cycle.

Example 2

Creation of the SwissProt/RefSeq Proteome Design

A set of human protein sequences was retrieved from UniProt (uniprot.org on the World Wide Web), consisting of 40,035 protein sequences, totaling 23,843,970 amino acids. Due to the large content size, several filtering sets were implemented to reduce the content size, enriching for more informative oligopeptides. The first step was to mask the protein sequences for low-complexity regions. This was done using the publicly available segmasker application (v1.0.0 from blast 2.2.23 package) from NCBI. The default parameters were used to mask low-complexity regions; a total of 2,258,766 aa were masked. A custom perl script was used to generate 16-mer oligopeptides from each protein sequence, at an interval of 6 aa. The number of synthesis cycles necessary to synthesize each oligopeptide was evaluated using the following amino acid sequence: A, R, N, D, C, E, Q, G, H, I, L, K, M, F, P, S, T, W, Y, V. Oligopeptides that could not synthesized using 10 repetitions of the preceding sequence were truncated to a minimum length of 10 aa. If they still could not be synthesized at that minimal length, the oligopeptide was discarded. For this set of protein sequences, only 5 oligopeptides were discarded for length consideration, because the full protein sequence was shorter than 10 amino acids. A total of 641,066 oligopeptides were discarded due to low-complexity masking. An additional 761 oligopeptides were discarded because they contained codes for non-standard amino acids. After discarding these 641,832 oligopeptides, a set of 3,288,695 oligopeptides remained. With these oligopeptide deletions, only 85 proteins were completely eliminated from the CCDS dataset. This set of oligopeptides contained 1,462,415 unique oligopeptides and 684,075 oligopeptides shared by two or more proteins. These shared oligopeptides sequences were placed on the array only once, and a correspondence key generated to indicate the original sequence identifiers and positions for later data analysis.

Roche NimbleGen's array layout software, ArrayScribe, was used to randomly distribute the final 2,146,490 oligopeptides across the array design template. The final array design consisted of three 1,050 feature wide×1,400 feature high subarrays. Each feature was 13.67 µm square. The oligopeptides were arranged randomly in a checkerboard fashion in each subarray, such that a maximum of 735,000 oligopeptides could be synthesized on each subarray. After placement of the oligopeptides, a series of files was produced to direct the light-mediated deprotection of individual features for each amino acid synthesis cycle.

Example 3

Synthesis, Binding and Analysis of CCDS Proteome Arrays

Arrays were synthesized on Greiner Bio One HTA 3D amino slides. Briefly, 400 µl of an amino acid (diluted to 60 mM in Dimethylformamide (DMF)) was delivered to a reaction vessel and activated with 200 µl of activator (60 mmol HBTU, 60 mmol HOBt in DMF) and 200 µl base (0.27M DIPEA in DMF). The mixture was mixed via bubbling through air. Activation proceeded for 5 minutes. The entire activated amino acid mixture was delivered to the slide in the flow cell and allowed to couple for 1 minute. After coupling, 3000 µl of 1-Methyl-2-pyrrolidinone (NMP) was washed over the array, before flowing 1000 µl of exposure solvent (0.01% hydroxylamine in NMP) to wash and cover the active array surface. Features were then deprotected by removing the NPPOC protecting group from the amino terminus of the bound amino acid. Deprotection occurred in exposure solvent (see above) through the delivery of 365 nm UV light from a mercury-xenon lamp at an approximate power of 161 mw/cm$^2$ for 60 seconds. Initial coupling of a 6-hexanoic acid linker as above was followed by 143 sequential peptide coupling and directed photodeprotection steps to build the desired peptide sequences. Each peptide had an additional Serine residue at each end in order to improve hydrophilicity of the support bound peptide and enable easy access of antibodies.

After completion of synthesis arrays were washed in 3000 µl of MeOH, and dried with argon. Peptide side-chain removal was accomplished by immersion in a 95% TFA/4.5% H$_2$O/0.5% Triisopropylsilane solution for 30 minutes at room temperature. Arrays were then washed twice in copious amounts of MeOH, rinsed with H$_2$O, and dried with an argon jet.

Binding of arrays was proceeded by washing of arrays in 1×TBSTT (0.055% Tween-20 and 0.22% Triton X-100) for 2 minutes, followed by washing in 1×TBS for 2 minutes. After washes, arrays were incubated overnight (~16 hours) in binding solution (22.5 µl 1×TBS, 18 µl DiH$_2$O, 4.5 µl 5% alkali-soluble Casein) with 1:15000 final dilution of polyclonal anti-ADA produced in rabbit (Sigma-Aldrich HPA001399 0.19 mg/ml), polyclonal anti-PAPOLA produced in rabbit (Sigma-Aldrich HPA001788, 0.05 mg/ml) and monoclonal anti-poly-Histidine (Sigma-Aldrich H1029, 0.25 mg/ml) produced in mouse. Incubation occurred at ambient temperature with mixing via a Roche NimbleGen Hybridization System.

After removal from primary incubation, arrays were washed twice for 2 minutes each in 1×TBSTT and once in 1×TBS for 2 minutes. Arrays were then placed in an opaque plastic staining jar containing 75 ml binding solution (see above) containing a 1:10000 final dilution of donkey anti-rabbit IgG (Jackson ImmunoResearch 711-165-152, 1.5 mg/ml) Cy3-labeled secondary antibody for detection of bound ADA and PAPOLA and a 1:10000 dilution goat anti-mouse (Invitrogen A10521, 2 mg/ml) Cy3-labeled secondary antibody. Incubation occurred with gentle shaking at ambient temperature for 3 hours.

After secondary binding, arrays were washed twice for 2 minutes in 1×TBSTT, rinsed with DiH₂O, and dried with an argon stream.

Arrays were scanned using a Roche NimbleGen MS200 scanner, in the 532 nm channel at a resolution of 2 μm. Images were analyzed using NimbleScan, raw intensities of the features were plotted vs. protein position using SignalMap software from Roche Nimblegen.

Example 4

Binding of Anti-PAPOLA Polyclonal Antisera to Oligopeptide Arrays

Targeted peptide arrays were designed utilizing similar tiling strategy and software as described in Example 1, and synthesized in similar fashion as detailed Example 3. The targeted arrays were designed from a target population of 52 proteins including the full PAPOLA protein sequence and an antigen subset (the "PA52 design"), tiled at single amino acid resolution (i.e., a 1 amino acid "step"). Binding experiments using ATLAS (Sigma-Aldrich) derived anti-PAPOLA polyclonal antibodies for primary antibody binding was performed as described in Example 3 above. Secondary antibody binding was performed using donkey anti-rabbit IgG Cy3-labeled secondary antibody for detection of bound PAPOLA antibodies.

Figure 3A:
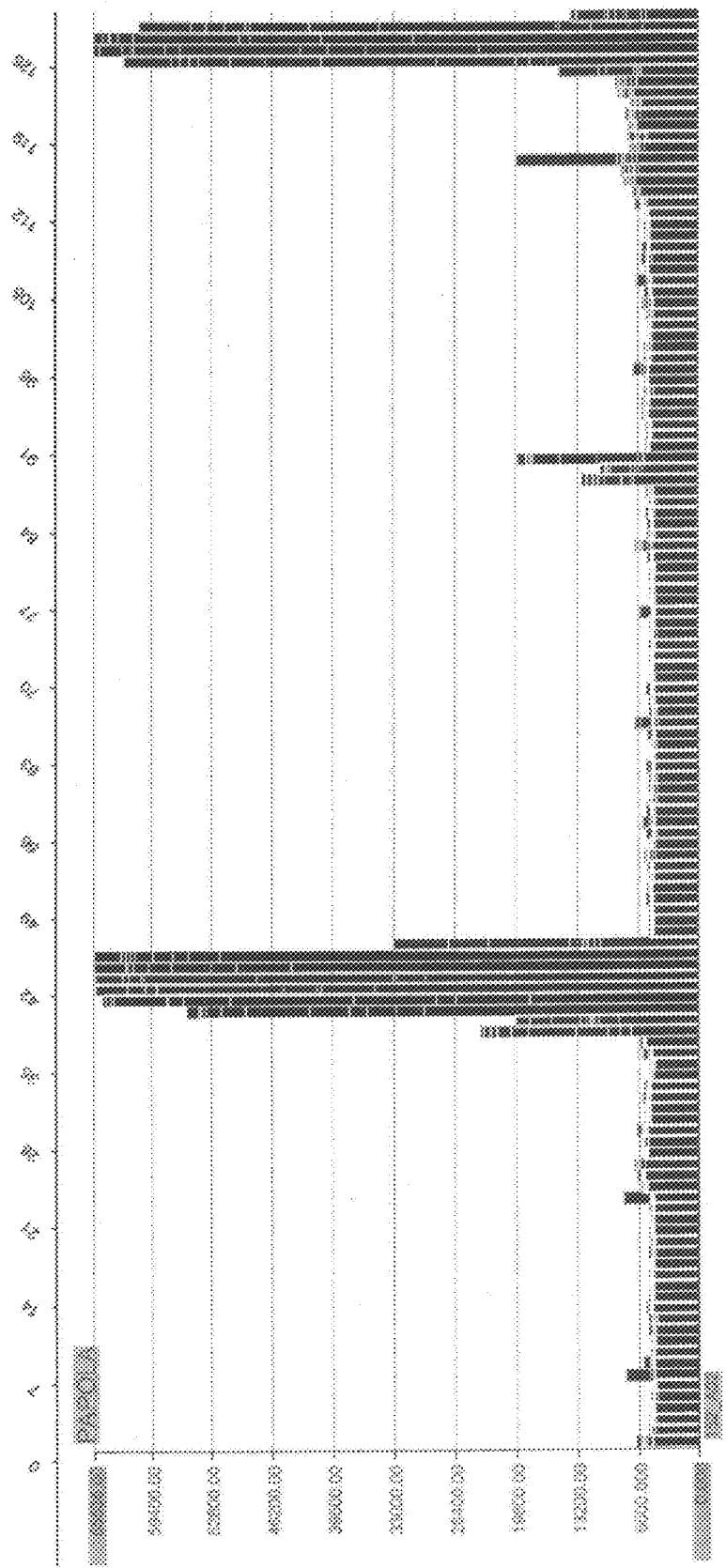
FIG. 3 provides examples of polyclonal anti-PAPOLA binding to "targeted" peptide array (FIG. 3A), the same array viewing binding to the full length PAPOLA protein (FIG. 3B), and binding to PAPOLA target on a full proteome array (FIG. 3C).

FIG. 3A shows the fluorescence detected using a PA52 design microarray for a target subset of PAPOLA protein comprised of approximately 140 amino acids, tiled at single amino acid resolution (1×10 tiling). This binding experiment resulted in identification of three potential epitopes:

```
                                           (SEQ ID NO: 2)
NSSGSSQGRNSPAPAVTA
(9 features, positions 38-46)

(SEQ ID NO: 3)
NAATKIPTPIVGV
(4 features, positions 126-129)

Possibly a third epitope at
                                           (SEQ ID NO: 4)
ATQPAISPPPKP
(3 features, positions 88-90).
```

FIG. 3B shows a trace of the same array (PA52 design), viewing the full length PAPOLA protein (approximately 730 amino acids), tiled at single amino acid resolution. When the data is examined at this level, three potential epitopes are again identified:

```
                                           (SEQ ID NO: 5)
NSSGSSQGRNSPAPAVTA
(9 features, positions 548-556)

(SEQ ID NO: 6)
NAATKIPTPIVGVK
(4 features, positions 637-640)

Possibly a third epitope at
                                           (SEQ ID NO: 7)
ATQPAISPPPKP
(3 features, positions 599-601)
```

Figure 3C:
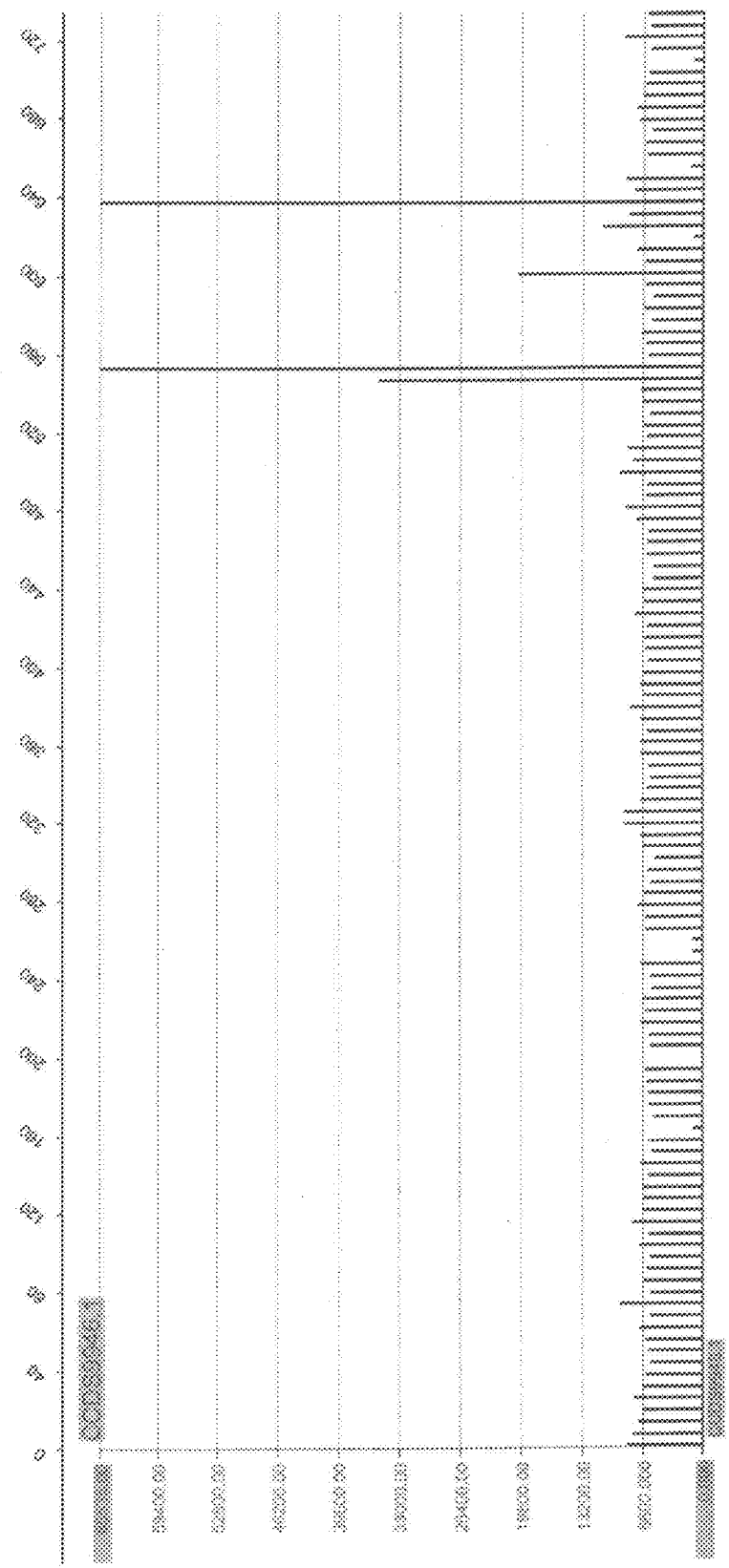

FIG. 3C shows an example of polyclonal anti-PAPOLA binding to PAPOLA target on a CCDS "full proteome" microarray designed and synthesized in similar fashion to Example 1 and Example 3 above. This oligopeptide microarray is a 6×12 design (i.e., 12-mer oligopeptides with a 6mer overlap or "step"). Identified epitopes from this experiment are:

```
                                           (SEQ ID NO: 8)
LNSSGSSQGRNSPAPAVT
(two features, position 547, 553)

(SEQ ID NO: 9)
NAATKIPTPIVG
(position 637)

Possibly a third epitope at
                                           (SEQ ID NO: 10)
QPAISPPPKP
(position 601).
```

Results of all three scans exemplified in FIGS. 3A-C are found in Table 1:

TABLE 1

|  | Epitope | Epitope | Epitope |
|---|---|---|---|
| PA52_sub 1aa_tile | NSSGSSQGRNSPAPAVTA (SEQ ID NO: 2) | NAATKIPTPIVGV (SEQ ID NO: 3) | ATQPAISPPPKP (SEQ ID NO: 4) |
| PA52_full 1aa_tile | NSSGSSQGRNSPAPAVTA (SEQ ID NO: 5) | NAATKIPTPIVGVK (SEQ ID NO: 6) | ATQPAISPPPKP (SEQ ID NO: 7) |
| CCDS_proteome_6aa_tile | LNSSGSSQGRNSPAPAVT (SEQ ID NO: 8) | NAATKIPTPIVG (SEQ ID NO: 9) | QPAISPPPKP (SEQ ID NO: 10) |

From this, one can discern that the full proteome design of the present invention, using a 6×12 tiling design, can detect essentially the same potential epitopes for anti-PAPOLA binding as are demonstrated by arrays with significantly less content and much higher amino acid resolution. This utility of a full proteome array provides unprecedented opportunity to screen for antibody binding across an essentially complete proteome, and allows for determination of the epitopes against which an antibody binds. Further, this provides opportunity to determine if a particular antibody exhibits high cross-reactivity to a large number of epitopes throughout the proteome, or if the antibody's reactivity is more specifically confined to expected epitopes or targets.

Example 5

Synthesis of the Antigen Sequences of 52 Selected Antibodies

Fifty-two antibodies were selected from the Human Protein Atlas database (proteinatlas.org on the World Wide Web). The respective antigen sequences were synthesized according to Example 3 in 164 successive synthesis cycles as 10-mer peptides with an overlap of 9 amino acids. In some cases, the overlap was shorter, but none was less than 6 amino acids. Deprotected oligopeptide arrays were incubated with mixtures of antibodies at dilution factors according to the data sheet recommendation for WESTERN analysis in the manufacturer's recommended buffer and their binding epitopes were determined as the highest intensity signals upon fluorescent labeling with an anti-rabbit secondary antibody (see FIG. 4). In some cases, the arrays were washed with buffer containing 0.1% SDS in order to remove non-specific bound antibodies.

Example 6

Sensitivity Titration of Anti-PAPOLA in Buffer

Figure 6:
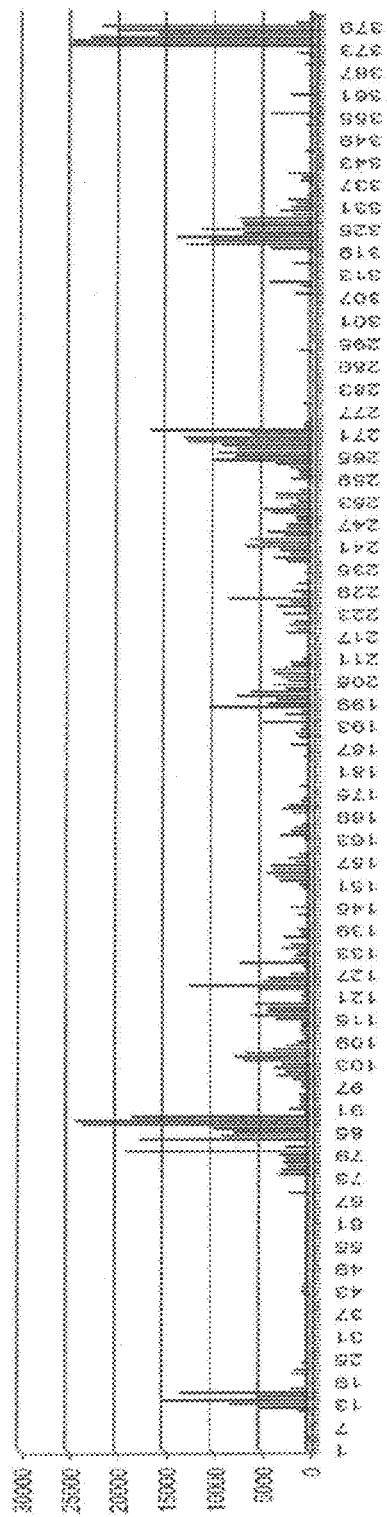
FIG. 6 shows binding of an isolated IgG pool from a colorectal cancer serum sample to an array with approximately 40,000 12-mer peptides with an 11-mer overlap.

A peptide array manufactured in similar fashion as described in Example 1 and Example 3 above was incubated with escalating dilutions of the anti-PAPOLA antibody (PolyA Polymerase alpha, HPA001788), from 1:10,000 up to 1:240,000 in discrete sub-arrays formed by a Roche Nimblegen 12-plex sample chamber assembly. Staining and washing was performed as described above. FIG. 6 depicts the binding results for various dilutions of antibody, focusing on amino acid positions 126-129 of the PAPOLA antigen sequence. As depicted in FIG. 5, raw data after fluorescent scanning with a Roche Nimblegen MS 200 micro array scanner revealed the epitopes clearly visible even at the highest dilution, comparing to an antibody concentration of about 200 pg/mL, with a relative signal to noise ratio of 4:1.

Example 7

Oligopeptide Array Binding With A Serum Sample

An isolated IgG pool from a colorectal cancer serum sample was bound to an oligopeptide array containing approximately 40,000 12-mer oligopeptide features with an 1'-mer overlap. The serum sample was from a serum bank containing clinically characterized sera for different diseases. Samples from cancer patients were screened with an anti-p53 assay for high-titer sera. From a high-titer serum, IgG was isolated by standard procedures. A dilution (10 μg/ml) of this preparation was used for binding studies. Incubation of array with sample was performed overnight in a Maui/X1 mixer at room temperature. After incubation, the array was washed for two minutes each with TBSTT, TBST/TBS, and $H_2O$. Secondary antibody staining was performed using Goat(anti) Human (Jackson ImmunoResearch) labeled with Cy3 dye, (1:12,500) for 3 hours. The array was washed for two minutes each with TBSTT, TBST/TBS, and $H_2O$, dried and scanned in an MS200 scanner.

FIG. 6 shows the data generated by this scan. The data shows intense binding to the peptides representing P-53 protein, a known antigen in autoimmunity in cancer. This data trace also suggests that there are multiple binding events from many auto-antibodies in a single patient. In FIG. 6, the oligopeptides that are tiling positions 10-40 (approximately) are peptides that represent a known antigen. In ELISA testing, the sample used in FIG. 6 tested positive against that specific antigen; however, FIG. 6 demonstrates significant binding events at other loci within the P-53 protein. In fact, the other loci in this patient sample show significantly higher intensity binding than the binding of the known antigenic site.

In current practice, a patient who is already showing signs of illness (e.g., a patient who is already suspected of having cancer) may demonstrate auto-immunity to certain known antigens, which is confirmatory of the cancer diagnosis. However, if the currently known auto-immunity test comes back negative, the clinician is still not well informed as the autoimmunity antibodies may not be highly reactive to the known (currently used) antigens. Autoimmune antibodies can be found in cancer patients almost all the time at a stage when the patient is already presenting with clinical signs of illness; however, current tests may not be as complete for diagnosis or early detection as a tool that provides a broader look at the binding events, such as the present invention. These data demonstrate that looking at autoimmune antibody "fingerprints" across a broader spectrum of potential antigenic sites may improve the prognostic value of autoimmunity tests.

Example 8

Serum Binding Assay Using Peptide Proteome Array

This process is identical to procedure in Example 3, with the following exceptions:
1. Anti-ADA, PAPOLA, and poly-Histidine antibodies are replaced with a 1:20 dilution of serum sample.
2. Secondary binding is performed with appropriate secondary antibody (i.e. species-specific)
3. Post-secondary binding washes will include 0.2% SDS wash for 2 hours or longer Arrays of specified design (CCDS proteome, RefSeq proteome, SwissProt proteome) are synthesized and side-group deprotected as above.

Binding of arrays is proceeded by washing of arrays in 1×TBSTT (0.055% Tween-20 and 0.22% Triton X-100) for 2 minutes, followed by washing in 1×TBS for 2 minutes. After washes, arrays are incubated overnight (~16 hours) in binding solution (22.5 μl 1×TBS, 18 μl $DiH_2O$, 4.5 μl 5% alkali-soluble Casein) with 1:20 final dilution of serum sample. Incubation occurs at ambient temperature with mixing via a Roche Nimblegen Hybridization System.

After removal from primary incubation, arrays are washed twice for 2 minutes each in 1×TBSTT and once in 1×TBS for 2 minutes. Arrays are then placed in an opaque plastic staining jar containing 75 ml binding solution (see above) containing a 1:10000 final dilution of appropriate, species-specific, fluorescently labeled secondary antibody. Incubation occurs with gentle shaking at ambient temperature for 3 hours.

After secondary binding, arrays are washed twice for 2 minutes in 1×TBSTT. Arrays are then subjected to stringent wash in 0.2% SDS for 2 hours with gentle shaking, prior to final rinse with $DiH_2O$ and drying with argon.

Arrays are scanned using a Roche Nimblegen MS200 scanner, in the appropriate channel (e.g. 532 nm, 635 nm) at a resolution of 2 μm. Images are analyzed using NimbleScan, raw intensities of the features are plotted vs. protein position using SignalMap.

Example 9

Binding of Anti-ADA Polyclonal Antisera to Oligopeptide Arrays

Figure 7B:
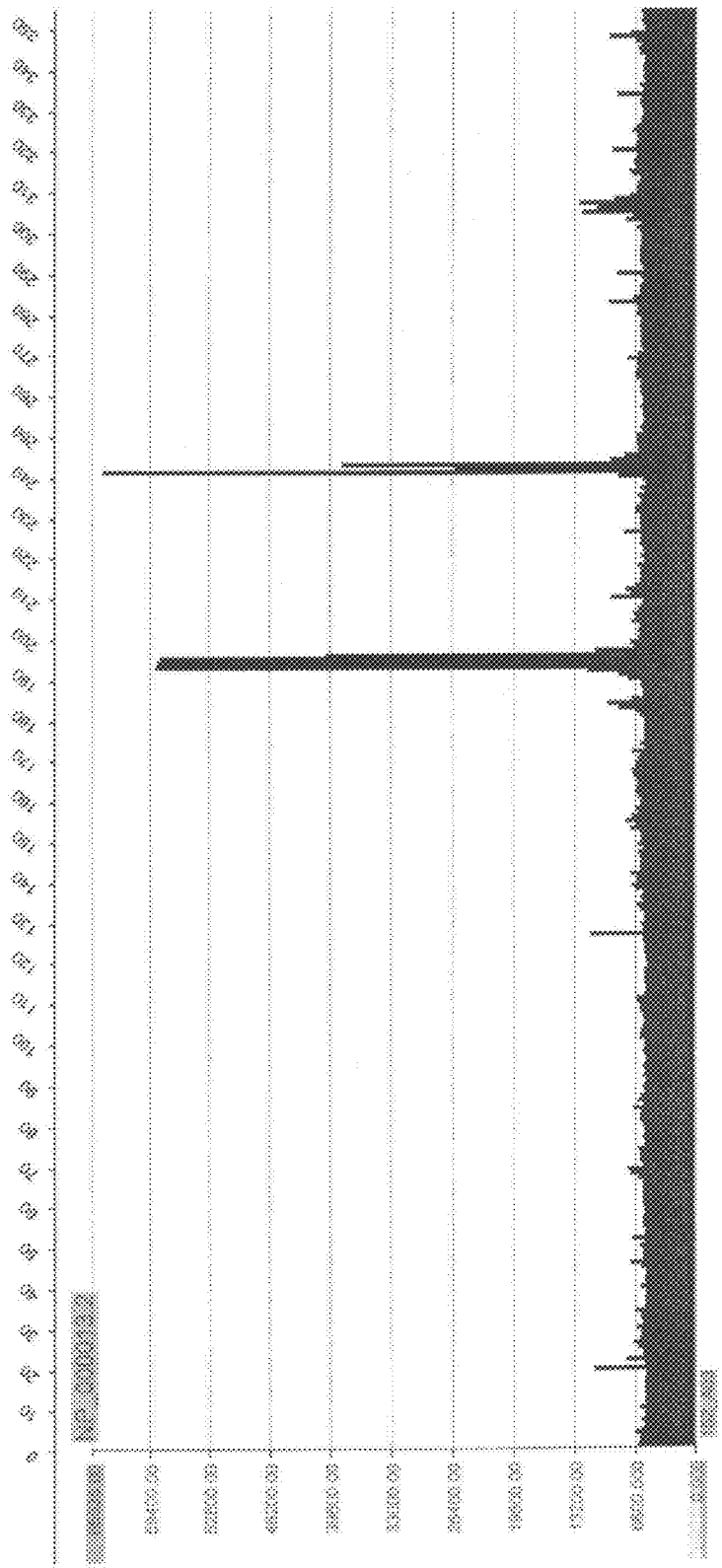
FIG. 7 provides examples of polyclonal anti-ADA binding to "targeted" peptide array (FIG. 7A), the same array viewing binding to the full length ADA protein (FIG. 7B), and binding to ADA target on a full proteome array (FIG. 7C).

Targeted peptide arrays were designed utilizing similar tiling strategy and software as described in Example 1, synthesized and binding experiments performed as described in Example 3. FIGS. 7A, 7B and 7C show the results of binding experiments using ATLAS (Sigma-Aldrich) derived anti-ADA polyclonal antibodies for primary antibody binding as described in Example 3 above. Secondary antibody binding was performed using donkey anti-rabbit IgG Cy3-labeled secondary antibody for detection of bound ADA antibodies.

FIG. 7A shows the fluorescence detected using a PA52 design microarray for a target subset of ADA protein comprised of approximately 140 amino acids, tiled at single amino acid resolution (1×10 tiling). This binding experiment resulted in identification of two potential epitopes:

```
                                                (SEQ ID NO: 11)
SLLPGHVQAYQEAV
(5 features, positions 9-13)

(SEQ ID NO: 12)
HTLEDQALYNRLQEN
(6 features, positions 58-63)
```

FIG. 7B shows a trace of the same array (PA52 design), viewing the full length ADA protein, tiled at single amino acid resolution. When the data is examined at this level, two potential epitopes are again identified:

```
                                                (SEQ ID NO: 13)
SLLPGHVQAYQEAV
(5 features, positions 192-196)

(SEQ ID NO: 14)
HTLEDQALYNRL
(4 features, positions 241-243)
```

FIG. 7C shows an example of polyclonal anti-ADA binding to ADA target on a CCDS "full proteome" microarray designed and synthesized in similar fashion to Example 1 and Example 3 above. This oligopeptide microarray is a 6×12 design (i.e., 12-mer oligopeptides with a 6mer overlap or "step"). The identified epitope from this experiment is:

```
                                                (SEQ ID NO: 15)
LLPGHVQAYQEA
(1 feature, position 193)
```

The expected epitope binding at approximately position 241 was missing in the full proteome binding experiment; however, this was readily explained by the fact that the features at and around position 241 were occluded by a slide logo mark indicating the slide manufacturer. The feature that was expected to show a peak at position 241 instead showed an actual drop below background levels, thus demonstrating that the feature was compromised because of the logo position.

From these data, one can discern that the full proteome design of the present invention, using a 6×12 tiling design, can detect essentially the same potential epitopes for anti-ADA binding as are demonstrated by arrays with significantly less content and much higher amino acid resolution.

Example 10

Binding of a Monoclonal Anti-Poly-Histidine Antibody to Full Proteome Array

FIG. 8 shows an example of monoclonal anti-poly-Histidine antibody binding to a potential epitope on a CCDS "full proteome" microarray. This microarray was designed and synthesized and binding experiments conducted as described in Example 1 and Example 3 above.

This oligopeptide microarray is a 6×12 design (i.e., 12-mer oligopeptides with a 6-mer overlap or "step"). The identified epitope from FIG. 8 is:

```
                                                (SEQ ID NO: 16)
HFQHHHHH
(1 feature, position 511)
```

This is only one example from this binding experiment: there were numerous other examples in the design where the monoclonal anti-poly-Histidine antibody bound other peptides with poly-Histidine stretches (data not shown). This binding experiment demonstrated that a full proteome array can readily be used for binding of monoclonal antibodies as well as polyclonal antibodies.

What is claimed is:

1. A microarray comprising at least 50,000 oligopeptide features per cm$^2$ wherein the features represent between about 90% and 100% of a target proteome, the target selected from a virus and an organism, and wherein at least a portion of the features comprise oligopeptides having a terminal 2-(2-nitro-4-benzoyl-phenyl)-propoxycarbonyl(benzoyl-NPPOC)-protected tyrosine residue.

2. The microarray of claim 1, comprising at least 100,000 oligopeptide features per cm$^2$.

3. The microarray of claim 1, comprising at least 200,000 oligopeptide features per cm$^2$.

4. The microarray of claim 1, wherein the organism is human.

5. The microarray of claim 1, wherein substantially all of the oligopeptides are the same length.

6. The microarray of claim 1, wherein substantially all of the oligopeptides are 9 to 18 amino acid residues in length.

7. The microarray of claim 6, wherein substantially all of the oligopeptides are 10 to 15 amino acid residues in length.

8. The microarray of claim 7, wherein substantially all of the oligopeptides are 12 amino acid residues in length.

9. The microarray of claim 1, wherein each oligopeptide feature overlaps in amino acid sequence with the amino acid sequence of at least one other feature by at least 3 contiguous amino acid residues.

10. The microarray of claim 9, wherein each oligopeptide feature overlaps by at least 9 amino acid residues.

11. A method for synthesizing a microarray comprising at least 50,000 oligopeptide features per cm$^2$ wherein the features represent between about 90% and 100% of a target proteome, the target selected from a virus and an organism, the method comprising synthesizing the oligopeptide features on the microarray such that an oligopeptide feature overlaps in amino acid sequence with the amino acid sequence of at least one other oligopeptide feature by at least one amino acid residue, wherein at least a portion of the features comprise oligopeptides having a terminal 2-(2-nitro-4-benzoyl-phenyl)-propoxycarbonyl(benzoyl-NPPOC)-protected tyrosine residue.

12. The method of claim 11, wherein each oligopeptide feature overlaps in amino acid sequence with the amino acid sequence of at least one other oligopeptide feature by exactly 9 amino acid residues.

13. The microarray of claim 1, wherein the benzoyl-NPPOC is cleavably bound to the terminal tyrosine residue.

14. The microarray of claim 1, wherein the benzoyl-NPPOC is photolabile.

15. The microarray of claim 1, wherein an oligopeptide feature overlaps in amino acid sequence with the amino acid sequence of at least one other oligopeptide feature by exactly 9 amino acid residues.

16. The microarray of claim 1 wherein the microarray comprises tiled oligopeptide features, and wherein the oligopeptides represent portions of at least about 5,000 of the proteins expressed in a species.

17. The microarray of claim 16, wherein the oligopeptides represent portions of at least about 10,000 expressed proteins.

18. The microarray of claim 16, wherein the oligopeptides represent portions of at least about 20,000 expressed proteins.

19. The microarray of claim 16, wherein the oligopeptides represent portions of between about 5,000 and 50,000 expressed proteins.

20. The microarray of claim 15, wherein the species is human.

* * * * *